United States Patent
Mizzen et al.

(10) Patent No.: US 7,262,014 B2
(45) Date of Patent: Aug. 28, 2007

(54) IMMUNE RESPONSES AGAINST HPV ANTIGENS ELICITED BY COMPOSITIONS COMPRISING AN HPV ANTIGEN AND A STRESS PROTEIN OR AN EXPRESSION VECTOR CAPABLE OF EXPRESSION OF THESE PROTEINS

(75) Inventors: Lee A. Mizzen, Victoria (CA); N. Randall Chu, Victoria (CA); Huacheng Bill Wu, Victoria (CA)

(73) Assignee: Stressgen Biotechnologies Corporation, Victoria, British Columbia ( * ) Notice: Subject to any disclaimer, the term of this patent is extended or adjusted under 35 U.S.C. 154(b) by 336 days.

(21) Appl. No.: 10/938,695

(22) Filed: Sep. 10, 2004

(65) Prior Publication Data

US 2005/0037017 A1   Feb. 17, 2005

Related U.S. Application Data

(60) Division of application No. 10/289,760, filed on Nov. 7, 2002, now Pat. No. 6,900,035, which is a continuation of application No. 09/498,918, filed on Feb. 4, 2000, now Pat. No. 6,524,825, which is a continuation of application No. PCT/CA98/00246, filed on Mar. 20, 1998.

(60) Provisional application No. 60/054,835, filed on Aug. 5, 1997.

(51) Int. Cl.
   *C12Q 1/68* (2006.01)
(52) U.S. Cl. .................. 435/6; 435/69.1; 424/278.1
(58) Field of Classification Search .............. 435/6, 435/69.1; 424/278.1
   See application file for complete search history.

(56) References Cited

U.S. PATENT DOCUMENTS

| | | | |
|---|---|---|---|
| 4,716,038 A | 12/1987 | Stanford et al. | 424/92 |
| 4,724,144 A | 2/1988 | Rook et al. | 424/93 |
| 4,918,166 A | 4/1990 | Kingsman et al. | 530/350 |
| 5,114,844 A | 5/1992 | Cohen et al. | 435/7 |
| 5,348,945 A | 9/1994 | Berberian et al. | 514/21 |
| 5,504,005 A | 4/1996 | Bloom et al. | 435/253 |
| 5,578,300 A | 11/1996 | Schmidt et al. | 424/78.08 |
| 5,580,563 A | 12/1996 | Tam | 424/197 |
| 5,599,545 A | 2/1997 | Stanford et al. | 424/282.1 |
| 5,736,146 A | 4/1998 | Cohen et al. | 424/197.11 |
| 5,750,119 A | 5/1998 | Srivastava | 424/277.1 |
| 5,830,464 A | 11/1998 | Srivastava | 424/93.71 |
| 5,837,251 A | 11/1998 | Srivastava | 424/193.1 |
| 5,858,368 A | 1/1999 | Smith et al. | 424/192.1 |
| 5,935,576 A | 8/1999 | Srivastava | 424/184.1 |
| 5,948,646 A | 9/1999 | Srivastava | 435/69.3 |
| 5,961,979 A | 10/1999 | Srivastava | 424/193.1 |
| 5,985,270 A | 11/1999 | Srivastava | 424/93.71 |
| 5,997,873 A | 12/1999 | Srivastava | 424/193.1 |
| 6,007,806 A | 12/1999 | Lathe et al. | 424/93.2 |
| 6,007,821 A | 12/1999 | Srivastava et al. | 424/193.1 |
| 6,017,540 A | 1/2000 | Srivastava et al. | 424/193.1 |
| 6,017,544 A | 1/2000 | Srivastava | 424/277.1 |
| 6,030,618 A | 2/2000 | Srivastava | 424/184.1 |
| 6,048,530 A | 4/2000 | Srivastava | 424/193.1 |
| 6,130,087 A | 10/2000 | Srivastava et al. | 435/372.3 |
| 6,136,315 A | 10/2000 | Srivastava | 424/193.1 |
| 6,139,841 A | 10/2000 | Srivastava | 424/193.1 |
| 6,143,299 A | 11/2000 | Srivastava | 424/193.1 |
| 6,156,302 A | 12/2000 | Srivastava | 424/93.1 |
| 6,162,436 A | 12/2000 | Srivastava | 424/193.1 |
| 6,168,793 B1 | 1/2001 | Srivastava | 424/193.1 |
| 6,187,312 B1 | 2/2001 | Srivastava | 424/193.1 |
| 6,322,790 B1 | 11/2001 | Srivastava | 424/193.1 |
| 6,335,183 B1 | 1/2002 | Young et al. | 435/69.7 |
| 6,338,952 B1 | 1/2002 | Young et al. | 435/69.7 |

FOREIGN PATENT DOCUMENTS

| | | |
|---|---|---|
| EP | 0 262 710 | 4/1988 |
| EP | 0 322 990 | 7/1989 |

(Continued)

OTHER PUBLICATIONS

K. Suzue et al., "Adjuvant-free hsp70 fusion protein system elicits humoral and cellular immune responses to HIV-1 p. 24", *J. of Immunology*, 156:873-879 (1996).

(Continued)

*Primary Examiner*—Ali R. Salimi
(74) *Attorney, Agent, or Firm*—Fish & Richardson P.C.; Lee Crews

(57) ABSTRACT

This document describes compositions and methods for inducing an immune response (e.g., a cellular response such as a cell-mediated cytolytic immune response) to a human papillomavirus (HPV) antigen, which can be displayed by HPV or exhibited by infected cells (e.g., cells from cervical and other tumors). The HPV protein can be joined to a stress protein by chemical conjugation or noncovalently using linking moieties, or by fusion (e.g., a recombinant fusion protein). Also described are expression vectors containing sequences encoding HPV antigens and stress proteins, which can be introduced into cells of a subject or cells ex vivo. Also described are compositions that include a stress protein linked to an HPV antigen and another pharmacologically acceptable component and stress protein—HPV antigen fusions and conjugates. These compositions can be used to induce or enhance an immune response against HPV and cells that exhibit HPV antigens, including HPV-associated tumors.

15 Claims, 13 Drawing Sheets

FOREIGN PATENT DOCUMENTS

| | | |
|---|---|---|
| GB | 2 251 186 | 7/1992 |
| WO | WO85/05034 | 11/1985 |
| WO | WO88/00974 | 2/1988 |
| WO | WO88/05823 | 8/1988 |
| WO | WO88/06591 | 9/1988 |
| WO | WO89/12455 | 12/1989 |
| WO | WO90/15873 | 12/1990 |
| WO | WO91/02542 | 3/1991 |
| WO | WO91/15572 | 10/1991 |
| WO | WO92/08484 | 5/1992 |
| WO | WO92/08488 | 5/1992 |
| WO | WO93/17712 | 9/1993 |
| WO | WO94/03208 | 2/1994 |
| WO | WO94/29459 | 12/1994 |
| WO | WO95/24923 | 9/1995 |
| WO | WO95 31994 | 11/1995 |
| WO | WO96/10421 | 4/1996 |
| WO | WO96 19496 | 6/1996 |
| WO | WO96 26277 | 8/1996 |
| WO | WO97 06821 | 2/1997 |
| WO | WO9710000 | 3/1997 |
| WO | WO97/26910 | 7/1997 |
| WO | WO98/23735 | 6/1998 |
| WO | WO98/35705 | 8/1998 |

OTHER PUBLICATIONS

T. De Gruijl et al., "T cell proliferative responses against human papillomavirus type 16 E7 oncoprotein are most prominent in cervical intraepithelial neoplasia patients with a persistent viral infection", *J. of General Virology*, 77:2183-2191 (1996).

Hungarian Patent Office Novelty Search Report dated Sep. 12, 2002.

International Search Report (Application No. PCT/CA 98/00246) dated Sep. 30, 1998.

Berkner, "Development of Adenovirus Vectors for the Expression of Heterologous Genes," *BioTechniques* 6:616-629 (1988).

Cason et al., "Towards Vaccines Against Human Papillomavirus Type-16 Genital Infections," *Vaccine* 11:603-611 (1993).

Gupta et al., "Adjuvants for Human Vaccines—Current Status, Problems and Future Prospects," *Vaccine* 13:1263-1276 (1995).

Jenkins et al., "An Antigen Chimera of Poliovirus Induces Antibodies Against Human Papillomavirus Type 16," *J. Virol.* 64:1201-1206 (1990).

Miller et al., "Improved Retroviral Vectors for Gene Transfer and Expression," *BioTechniques* 7:980-990 (1989).

Nieland et al., "Isolation of an Immunodominant Viral Peptide that is Endogenously Bound to the Stress Protein GP96/GRP94," *Proc. Natl. Acad. Sci. USA* 93:6135-6139 (1996).

Power et al., "Induction of Protective Immunity in Rodents by Vaccination with a Prokaryotically Expressed Recombinant Fusion Protein Containing a Respiratory Syncytial Virus G Protein Fragment," *Virology* 230:155-166 (1997).

Schiller et al., "Papillomavirus Vaccines: Current Status and Future Prospects," *Adv. Dermatol.* 11:355-380 (1996).

Srivastava et al., "Heat Shock Proteins Transfer Peptides During Antigen Processing and CTL Priming," *Immunogenetics* 39:93-98 (1994).

Steller et al., "Human Papillomavirus Immunology and Vaccine Prospects," *Monog. Natl. Cancer Inst.* 21:145-148 (1996).

Sun et al., "An Antigenic Recombinant Fusion Protein from *Trichinella spiralis* Induces a Protective Response in BALB/c Mice," *J. Helmint.* 68:89-91 (1994).

Tindle et al., "Chimeric Hepatitis B Core Antigen Particles Containing B- and Th-Epitopes of Human Papillomavirus Type 16 E7 Protein Induce Specific Antibody and T-Helper Responses in Immunised Mice," *Virology* 200:547-557 (1994).

Tindle et al., "A Vaccine Conjugate of 'ISCAR' Immunocarrier and Peptide Epitopes of the E7 Cervical Cancer-Associated Protein of Human Papillomavirus Type 16 Elicits Specific Th1- and Th2-Type Responses in Immunized Mice in the Absence of Oil-Based Adjuvants," *Clin. Exp. Immunol.* 101:265-271 (1995).

Tindle et al., "Human Papillomavirus Vaccines for Cervical Cancer," *Curr. Opin. Immunol.* 8:643-650 (1996).

Wang et al., "Second-Generation Adenovirus Vectors," *Nature Medicine* 2:714-716 (1996).

Wu et al., "Engineering an Intracellular Pathway for Major Histocompatibility Complex Class II Presentation of Antigens," *Proc. Natl. Acad. Sci. USA* 92:11671-11675 (1995).

Agranovsky et al., "Putative 65 kDa Protein of Beet Yellows Closterovirus Is a Homologue of HSP70 Heat Shock Proteins," J. Mol. Biol., 217:603-610 (1991).

Ardeshir et al., "A 75 Kd Merozoite Surface Protein of Plasmodium Falciparum which is Related to the 70 kd Heat-Shock Proteins," EMBO J., 6(2):493-499 (1987).

Arnosti et al., "Characterization of heat shock in *Bacillus subtilis*," J. Bact., 168(3):1243-1249 (Dec. 1986).

Arrigo and Welch, "Characterization and Purification of the Small 28,000-Dalton Mammalian Heat Shock Protein", J. Biol. Chem., 262(32):15359-15369 (1987).

Barrios et al., "Heat shock proteins as carrier molecules: in vivo helper effect mediated by *Escherichia coli* GroEL and DnaK proteins requires cross-linking with antigen," Clin. Exp. Immunol., 98:229-233 (1994).

Barrios et al., "Mycobacterial heat-shock proteins as carrier molecules. II: The use of the 70-kDa mycobacterial heat-shock protein as carrier for conjugated vaccines can circumvent the need for adjuvants and Bacillus Calmette Guerin priming," Eur. J. Immunol., 22:1365-1372 (1992).

Beech et al., "CD4+ Th2 cells specific for mycobacterial 65-kilodalton heat shock protein protect against pristane-induced arthritis," J. Immunol. 159:3692-3697 (1997).

Bertelli et al., "BCG-Induced Resistance in *Trypanosoma cruzi* Experimental Infections," Tropenmed Parasitol, 32:93-96 (1981).

Birk et al., "T-cell autoimmunity in type 1 diabetes mellitus," Curr. Opin. Immunol., 5:903-909 (1993).

Blachere et al., "Heat Shock Protein-Peptide Complexes, Reconstituted in Vitro, Elicit Peptide-specific Cytotoxic T Lymphocyte Response and Tumor Immunity," J. Exp. Med. 186(8):1315-1322 (Oct. 20, 1997).

Blander and Horwitz, "Major Cytoplasmic Membrane Protein of Legionella Pneumophila, a Genus Common Antigen and Member of the hsp 60 Family of Heat Shock Proteins, Induces Protective Immunity in a Guinea Pig Model of Legionnaires' Disease," J. Clin. Invest., 91:717-723 (1993).

Borysiewicz et al, "A recombinant vaccinia virus encoding human papillomavirus types 16 and 18, E6 and E7 proteins as immunotherapy for cervical cancer," Lancet, 347:1523-27 (1996).

Butini et al., "Comparative Analysis of HIV-specific CTL Activity in Lymphoid Tissue and Peripheral Blood," J. Cell Biochem. Suppl. 18B Abstract J306 (1994).

Cain and Howett, "Preventing cervical cancer," SCIENCE, 288:1753-54 (2000).

Cassell et al., "A Phase II Study on the Postsurgical Management of Stage Malignant Melanoma With a Newcastle Disease Virus Oncolysate," CANCER, 52:856-860 (Sep. 1983).

Cassell et al., "Viral Oncolysate in the Management of Malignant Melanoma, I. Preparation of the Oncolysate and Measurement of Immunologic Responses" CANCER, 40:672-679 (Aug. 1977).

Catelli et al., "The common 90-kd protein component of non-transformed '8S' steroid receptors is a heat-shock protein", Embo J., 4(12):3131-3135 (1985).

Chandrasekhar et al., "Purification and Properties of the groES Morphogenetic Protein of *Escherichia coli*", J. Biol. Chem., 261(26):12414-12419 (1986).

Cohen et al., "Immunity to 60 kDa heat shock protein in autoimmune diabetes," Diab. Nutr. Metab., 9(4):229-232 (1996).

Cohen, "Jitters jeopardize AIDS vaccine trials ," SCIENCE, 262: 980-981 (1993).

Dahlseid et al., "PBP74, a new member of the mammalian 70-kDa heat shock protein family, is a mitochondrial protein," Mol Biol Cell. 5(11):1265-1275 (1994).

De Velasco et al., "Synthetic Peptides Representing T-Cell Epitopes Act as Carriers in Pneumococcal Polysaccharide Conjugate Vaccines," Infect. & Immun., 63:961-968 (1995).

Del Guidice, "Hsp70: a carrier molecule with built-in adjuvanticity," EXPERIENTIA, 50:1061-1066 (1994).

Del Guidice et al., "Heat shock proteins as "super"-carriers for sporozoite peptide vaccines?", Research in Immunol., 162:703-707 (1991).

Del Guidice et al., "Priming to Heat Shock Proteins in Infants Vaccinated against Pertussis," J. Immunol., 150(5):2025-2032 (1993).

DeNagel et al., "Heat shock proteins in Immune Responses," Crit. Rev. Immunol., 13(1):71-81 (1993).

Doherty et al, Evasion of host immune responses by tumours and viruses, "Vaccines against virally induced cancers," Wiley, Chicester (Ciba Foundation Symposium 187), pp. 245-260. See p. 245, Abstract , 1994.

DuBois et al., "Isolation of a Tumor-Associated Transplantation Antigen (TATA) From an SV40-Induced Sarcoma. Resemblance to the TATA of Chemically Induced Neoplasms," Int. J. Cancer, 34:561-566 (1984)*.

Dubois et al., "Protective immunization of the squirrel monkey against asexual blood stages of Plasmodium falciparum by use of parasite protein fractions," Proc. Natl. Acad. Sci., 81:229-232 (1984).

Elias et al., "Induction and therapy of autoimmune diabetes in the non-obese diabetic (NOD/Lt) mouse by a 65-kDa heat shock protein," Proc. Natl. Acad. Sci. USA, 87:1576-1580 (1990).

Falk et al., "Cell Mediated Immunity to Human Tumors," Arch. Surg., 107:261-265 (Aug. 1973).

Ferrero et al., "The GroES homolog of Helicobacter pylori confers protective immunity against mucosal infection in mice," Proc. Natl. Acad. Sci. USA, 92:6499-6503 (1995).

Flaherty et al., "Three-dimensional Structure of the ATPase Fragment of a 70K Heat-Shock Cognate Protein," NATURE 346:623-628, 1990.

Fox, "No Winners Against AIDS", BIOTECHNOLOGY, 12:128 (1994).

Friedland et al., "Mycobacterial 65-kD heat shock protein induces release of proinflammatory cytokines from human monocytic cells," Clin. Exp. Immunol., 91:58-62 (1993).

Galloway, "Papillomavirus oncoproteins as vaccine candidates," LANCET, 347:1498-99 (1996).

Gomes et al., "Heat shock protein synthesis during development in Caulobacter crescentus," J. Bact., 168(2):923-930 (Nov. 1986).

Gomez et al., "Vaccination with Recombinant Heat Shock Protein 60 from Histoplasma capsulatum Protects Mice against Pulmonary Histoplasmosis," Infect. & Immun., 63:2587-2595 (1995).

Haanen et al., "Selection of a human T helper type 1-like T cell subset by mycobacteria," J. Exp. Med., 174:583-592 (1991).

Haghbin et al., "Immunotherapy with Oral BCG and Serial Immune Evaluation in Childhood Lymphoblastic Leukemia Following Three Years of Chemotherapy," CANCER, 46:2577-2586 (Dec. 1980).

Hastie et al., "HSP27 Elevated in Mild Allergic Inflammation Protects Airway Epithelium from H2SO4 Effects," Am J. Physiol., 273 (Lung Cell. Mol. Physiol. 17):L401-L409 (1997).

Haynes, "Scientific and Social Issues of Human Immunodeficiency Virus Vaccine Development", SCIENCE, 260:1279-1286 (1993).

Hudson et al., "Active Specific Immunotherapy for Ovarian Cancer," The Lancet, 2:877-879 (Oct. 23, 1976).

Hughes et al., "A Study in Clinical Cancer Immunotherapy," CANCER, 26:269-278 (Aug. 1970).

Humphrey et al., "Adjuvant Immunotherapy for Melanoma," J. of Sur. Oncol., 25:303-305 (1984).

Hunt and Calderwood, "Characterization and Sequence of a Mouse hsp70 Gene and Its Expression in Mouse Cell Lines," GENE 87:199-204 (1990).

Husson and Young, "Genes for the major protein antigens of Mycobacterium tuberculosis: The etiologic agents of tuberculosis and leprosy share an immunodominant antigen," Proc. Natl. Acad. Sci. USA, 84:1679-1683 (1987).

Huygen et al., "Spleen cell cytokine secretion in Mycobacterium bovis BCG-infected mice," Infection and Immunity, 60(7):2880-2886 (1992).

Jacquier-Sarlin, "Protective effects of hsp70 in inflammation," EXPERIENTIA, 50(11-12):1031-1038 (1994).

Jarecki-Black et al., "The Effect of BCG-Vaccine Upon Experimental Visceral Leishmaniasis in Hampsters," Ann. Clin. Lab. Sci., 14:464-466 (1984).

Jindal, "Heat Shock Proteins: Applications in health and disease," Trends in Biotech, 14(1):17-20, 1996.

Jondal et al., "MHC Class I-Restricted CTL Responses to Exogenous Antigens," IMMUNITY 5:295-203 (Oct. 1996).

Kaufmann et al., "Enumeration of T cells reactive with Mycobacterium tuberculosis organisms and specific for the recombinant mycobacterial 64-kDa protein", Eur. J. Immunol., 17:351-357 (1987).

Kaufmann et al., "Heat-shock protein 60: implications for pathogenesis of and protection against bacterial infections," Immunological Reviews, 121:67-90 (1991).

Kiessling et al., "Role of hsp60 during autoimmune and bacterial inflammation," Immunological Reviews, 121:91-111 (1991).

Kimmig and Wenk, "Suppression of Parasitaemia from Litomosoides carinii by Immunisation with BCG and Microfilariae," Z. Parasitenkd, 67:317-327 (1982).

Konen-Waisman et al., "Self and Foreign 60-Kilodalton Heath Shock Protein T Cell Epitope Peptides Serve As Immunogenic Carriers for a T Cell-Independent Sugar Antigen," Journ. Immunol., 154:5977-5985 (1995).

La Thangue and Latchman, "A Cellular Protein Related to Heat-Shocked Protein 90 Accumulates during Herpes Simplex Virus Infection and Is Overexpressed in Transformed Cells," Experimental Cell Research, 178:169-179 (1988).

Lamb et al., "Stress Proteins may Provide a Link Between the Immune Response to Infection and Autoimmunity", Int'l. Immun., 1(2):191-196 (1989).

Layton et al., Induction of HIV-Specific Cytotoxic T lymphocytes In Vivo with Hybrid HIV-1`V3:Ty-Virus-Like-Particles, J. Immunology, 151(2):1097-1107 (Jul. 1993).

Leung et al., "The immunobiology of heat shock proteins," J. Investig. Allergol. Clin. Immunol., 1(1):23-30, (1991).

Levi et al., "Synthetic recombinant influenza vaccine induces efficient long-term immunity and cross-strain protection," VACCINE, 14:85-92 (1996).

Li and Srivastava, "Tumor Rejection Antigen gp96/grp94 is an ATPase: Implications for Protein Folding and Antigen Presentation," The Embo Journal, 12(8):3143-3151 (1993).

Lindquist and Craig, "The Heat-Shock Proteins," Annu. Rev. Genet., 22:631-677 (1988).

Lussow et al., "Mycobacterial heat-shocked proteins as carrier molecules," Eur. J. Immunol, 21:2297-2302 (1991).

Maytin, "Heat shock proteins and molecular chaperones: implications for adaptive responses in the skin," J. Invest. Dermatol., 104:448-455 (1995).

McCulloch et al., "Recurrent Malignant Melanoma: Effect of Adjuvant Immunotherapy on Survival," Can. Med. Assoc. J., 117:33-36 (Jul. 1977).

Miller et al., "Immunotherapy in autoimmune diseases," Curr. Opinion in Immun., 3:936-940 (1991).

Minowada et al., "Clinical implications of the stress response," J. Clin. Invest., 95:3-12 (1995).

Moré et al., Activation of cytotoxic T cells in vitro by recombinant gp96 fusion proteins irrespective of the 'fused' antigenic peptide sequence, Immunology Letters, 69:275-282 (1999).

Motal, "Glycosylphosphatidylinositol-linked Db does not induce an influenza-specific cytotoxic T lymphocyte response or recycle membrane-bound peptides," Eur. J. Immunol., 25:1121-1124 (1995).

Murphy and Lefford, "Host Defenses in Murine Malaria: Induction of a Protracted State of Immunity with a Formalin-Killed Plasmodium berghei Blood Parasite Vaccine," Infec. Immun., 22:798-803 (1978).

Murray et al., "Viral Oncolysate in the Management of Malignant Melanoma, II. Clinical Studies" CANCER, 40:680-686 (Aug. 1977).

Nadler et al., "Interaction of the Immunosupressant Deoxyspergualin with a Member of the Hsp70 Family of Heat Shock Proteins," SCIENCE, 258:484-486 (1992).

Noll and Autenrieti, "Immunity against *Yersinia enterocolitica* by Vaccination with *Yersinia* HSP60 Immunostimulating Complexes or *Yersinia* HSP60 plus Interleukin-12", Infect. & Immun., 64:2955-2961 (1996).

Oettgen and Old, "Chapter 6: The History of Cancer Immunotherapy." In Biologic Therapy of Cancer, De Vita, V.T., Hellman, S. and Rosenberg, S.A., eds., (London: J.B. Lippincott) pp. 98-103 (1991).

Orme et al., "Cytokine secretion by CD4 T lymphocytes acquired in response to Mycobacterium tuberculosis infection," J. Immunol., 151(1):518-525 (1993).

Palladino et al., "Expression of a Shared Tumor-Specific Antigen by Two Chemically Induced BALB/c Sarcomas," Cancer Research, 47:5074-5079 (Oct. 1987).

Peetermans et al., "Mycobacterial heat-shock protein 65 induces proinflammatory cytokines but does not activate human mononuclear phagocytes," Scan. J. Immunol., 39:613-617 (1994).

Pinskey et al., "Intravesical Administration of Bacillus Calmette-Guerin in Patients with Recurrent Superficial Carcinoma of the Urinary Bladder: Report of a Prospective, Randomized Trail," Cancer Treat. Rep., 69:47-53 (Jan. 1985).

Polla et al., "Heat shock proteins and inflammation," Current Topics in Microbiology and Immunology, 167:93-105 (1991).

Polla et al., "Regulation and functions of stress proteins in allergy and inflammation," Clinical and Experimental Allergy, 23:548-556 (1993).

Polla et al., "Spontaneous heat shock protein synthesis by alveolar macrophages in interstitial lung disease associated with phagocytosis of eosinophils," Eur. Respir. J., 6:483-488 (1993).

Rico et al., "Characterization of the Immunostimulatory Properties of *Leishmania infantum* HSP70 by Fusion to the *Escherichia coli* Maltose-Binding Protein in Normal nu/nu BALB/c Mice," Infection and Immunity 66:347-352 (Jan. 1998).

Roman et al., "Synthetic peptides non-covalently bound to bacterial hsp 70 elicit peptide-specific T-cell responses in vivo," IMMUNOLOGY, 88(4):487-492 (1992).

Shinnick et al., "The Etiologic Agents of Leprosy and Tuberculosis Share an Immunoreactive protein Antigen with the Vaccine Strain Mycobacterium bovis BCG", Infect. and Immun., 55(8):1932-1935 (1987).

Silverstein, "The History of Immunology," In Fundamental Immunology, 2.sup.nd Edition, Paul, W.E., ed., (NY:Raven Press), pp. 21, 23-24 (1989).

Sparks et al., "Immunology and Adjuvant Chemoimmunotherapy of Breast Cancer," Arch Surg, 111:1057-1062 (Oct. 1976).

Spencer et al., "Nonspecific Protection of Mice against Influenza Virus Infection by Local or Systemic Immunization with Bacille Calmette-Guerin," J. Infect, 171-175 (Aug. 1977).

Srivastava and Udono, "Heat Shock Protein-Peptide Complexes in Cancer Immunotherapy," Current Opinion in Immun., 6:728-732 (1994).

Srivastava and Old, "Individually Distinct Transplantation Antigens of Chemically Induced Mouse Tumors," Immunology Today, 9:78-83 (Mar. 1988).

Srivastava and Das, "The Serologically Unique Cell Surface Antigen of Zajdela Ascitic Hepatoma is Also Its Tumor-Associated Transplantation Antigen," Int. J. Cancer, 33:417-422 (1984).

Srivastava and Maki, "Stress-Induced Proteins in Immune Response to Cancer," Curr. Top. of Microbiol. Immunol., 167:109-123 (1991).

Srivastava et al., "Tumor Rejection Antigens of Chemically Induced Sarcomas of Inbred Mice," Proc. Natl. Acad. Sci., USA, 83:3407-3411 (May 1986).

Sturrock et al., "Attempts to Induce Resistance to *Schistosoma mansoni* and *S. haematobium* in Kenyan Baboons (*Papio anubis*) Using Non-Specific Immunostimulants," PARASITOLOGY, 90:101-110 (1985).

Suto and Srivastava, "A Mechanism for the Specific Immunogenicity of Heat Shock Protein-Chaperoned Peptides," Science 269:1585-1588 (Sep. 15, 1995).

Suzue et al., "Heat Shock Fusion Proteins as Vehicles for Antigen Delivery Into the Major Histocompatibility Complex Class I Presentation Pathway," Proc. Natl. Acad. Sci. USA, 94:13146-13151 (Nov. 1997).

Tamura et al., "Immunotherapy of Tumors with Autologous Tumor-Derived Heat Shock Protein Preparations," SCIENCE 278:117-120 (Oct. 3, 1997).

Thole et al., "Antigenic relatedness of a strongly immunogenic 65 kDA mycobacterial protein antigen with a similarly sized ubiquitous bacterial common antigen", Microbial Pathogenesis, 4:71-83 (1988).

Thole et al., "Characterization, Sequence Determination, and Immunogenicity of a 64-Kilodalton Protein of Mycobacterium bovis BCG Expressed in *Escherichia coli* K-12," Infection & Immunol., 55(6):1466-1475 (1987).

Udono et al., "Cellular Requirements for Tumor-Specific Immunity Elicited by Heat Shock Proteins: Tumor Rejection Antigen gp96 Primes CD8 T Cells in vivo," Proc. Natl. Acad. Sci. USA 91:3077-3081 (Apr. 1994).

Udono and Srivastava, "Heat Shock Protein 70-associated Peptides Elicit Specific Cancer Immunity," J. Exp. Med., 178:1391-1396 (Oct. 1993).

Ullrich et al., "A Mouse Tumor-Specific Transplantation Antigen is a Heat Shock-Related Protein," Proc. Natl. Acad. Sci., USA, 83:3121-3125 (May 1986).

van Eden et al., "Cloning of the mycobacterial epitope recognized by T lymphocytes in adjuvant arthritis", NATURE, 331(14):171-173 (1988).

Verdegaal et al., "Heat Shcok Protein 65 Induces CD62e, CD106, and CD54 on Cultured Human Endothelial Cells and Increases Their Adhesiveness for Monocytes and Granulocytes," Jour. Immunol., 157:369-376 (1996).

Vignola et al., "Increased expression of heat shock protein 70 on airway cells in asthma and chronic bronchitis," Am. J. Respir. Cell Mol. Biol., 13:683-691 (1995).

Vodkin and Williams, "A Heat Shock Operon in *Coxiella burnetii* Produces a Major Antigen Homologous to a Protein in Both Mycobacteria and *Escherichia coli*", J. of Bacteriology, 170(3):1227-1234 (1988).

Voellmy et al. "Isolation and functional analysis of a human 70,000-dalton heat shock protein gene segment," Proc Natl Acad Sci U S A. 82(15):4949-53 (1985).

Welch et al., "Biochemical characterization of the mammalian stress proteins and identification of two stress proteins as glucose- and Ca2+-ionophore-regulated proteins," J. Biol. Chem., 258(11):7102-7111 (1983).

Welch and Feramisco, "Purification of the Major Mammalian Heat Shock Proteins", J. Biol. Chem., 257(24):14949-14959 (1982).

Welch and Feramisco, "Rapid Purification of Mammalian 70,000-Dalton Stress Proteins: Affinity of the Proteins for Nucleotides", Mol. Cell. Biol., 5(6):1229-1237 (1985).

Young et al., "The 65kDa antigen of mycobacteria—a common bacterial protein?", Immunol. Today, 8(7-8):215-219 (1987).

Young et al., "Genes for the major protein antigens of the leprosy parasite mycobacterium leprae," NATURE, 316:450-452 (1985).

Young et al., "Stress proteins are immune targets in leprosy and tuberculosis," Proc. Natl. Acad. Sci. USA, 85:4267-4270 (1988).

Young, "Stress Proteins and Immunology," Annu. Rev. Immunol., 8:401-420 (1990).

Zhu et al., "Structural Analysis of Substrate Binding by the Molecular Chaperone DnaK," SCIENCE 272:1606-1614 (Jun. 14, 1996).

Zylicz et al., "The grpE Protein of *Escherichia coli*", J. Biol. Chem., 262(36):17437-17442 (1987).

Zylicz and Georgopoulos, "Purification and Properties of the *Escherichia coli* dnaK Replication Protein", J. Biol. Chem., 259(14):8820-8825 (1984).

IMMUNE RESPONSES AGAINST HPV ANTIGENS ELICITED BY COMPOSITIONS COMPRISING AN HPV ANTIGEN AND A STRESS PROTEIN OR AN EXPRESSION VECTOR CAPABLE OF EXPRESSION OF THESE PROTEINS

CROSS-REFERENCE TO RELATED APPLICATIONS

This application is a divisional (and claims the benefit of priority under 35 USC 120) of U.S. application Ser. No. 10/289,760, filed Nov. 7, 2002, now U.S. Pat. No. 6,900,035, which is a continuation of U.S. application Ser. No. 09/498,918, filed Feb. 4, 2000, now U.S. Pat. No. 6,524,825, which is a continuation of PCT international application no. PCT/CA98/00246, filed Mar. 20, 1998, which claims the benefit of U.S. provisional application Ser. No. 60/054,835, filed Aug. 5, 1997, all of which are herein incorporated by reference.

TECHNICAL FIELD

The present invention relates generally to methods and compositions involving linked stress proteins and human papillomavirus protein antigens for inducing an immune response against human papillomavirus protein antigens.

BACKGROUND OF THE INVENTION

Infection with human papillomaviruses (HPV) is common, and the viruses can be transmitted sexually. It is estimated that between 20 and 80% of sexually active adults are infected. While a majority of infections are asymptomatic, infection can lead to development of genital warts and cancer of the anogenital tract. Genital warts have a prevalence of 1-5% among adults. About one percent of women worldwide are afflicted with cervical cancer, which is the most common cause of death in women under the age of 50. Cervical cancer is strongly associated with HPV. Frazer, *Genitourin Med* 72:398-403 (1996).

Presently, no effective therapeutic compositions or prophylactic compositions, i.e., vaccines, against HPV are available, and there is, therefore, a need for development of effective compositions. The prospects for a conventional killed or live attenuated vaccine appear to be poor. According to Frazer, HPV has not yet been propagated in cell culture, and the tumor-promoting effects of HPV infection as well as the complete species specificity of HPV represent additional difficulties that cannot be readily overcome (Frazer, *Genitourin Med* 72:398-403 (1996)). It has been proposed that the observation that major capsid protein, when expressed in eukaryotic cells, forms virus-like particles that are immunogenic without adjuvant may provide a basis for the development of a vaccine (Christensen et al., *J Gen Virol* 75:2271-6 (1994); see also PCT/EP95/03974 and PCT/US95/12914).

HPV belongs to the A genus of the papovaviridae family which also includes SV40 and polyomavirus. More than 68 different types of HPV have been characterized that are structurally highly related but are less than 50% identical at the DNA sequence level. All known types are epitheliotropic viruses that infect specific types of epithelium and frequently produce epithelial proliferations. Several types were identified in common warts. Twenty-three types are known to infect the female and male anogenital tracts. Anogenital diseases caused by these types of HPV range from Condylomata acuminata to invasive squamous cell carcinoma. HPV DNA can be identified in over 80% of women with biopsy-confirmed squamous intraepithelial lesions or cervical intraepithelial neoplasia. A few particular types, including HPV 16, 18, and 31, are associated strongly with high grade squamous intraepithelial lesions and invasive cancer of the cervix, vulva, penis and anus (Lorincz et al., *Obstet Gynecol* 79:328-37 (1992)). According to Frazer, cervical cancer is 90-95% associated with HPV. Frazer, *Genitourin Med* 72:398-403 (1996). HPV is not only associated with cancer of the anogenital system, but is also present in pharyngeal, laryngeal and bladder carcinomas (Brachman et al., *Cancer Res* 52:4832-6 (1992); Rotola et al., *Int J Cancer* 52:359-65 (1992)). A recent study reported that HPV DNA was also present in 30% of lung carcinomas tested. Types identified included HPV 6, 11, 16, 18, 31 and 33 (Soini et al., *Thorax* 51:887-893 (1996)). Hence, HPV types most often associated with cancer are 6, 11, 16, 18, 31 and 33, of which HPV 16 and 18, which are detected in more than 90% of cervical carcinomas (van Driel et al., *Ann Med* 28:471-477 (1996)), have been investigated most thoroughly.

Papillomaviruses are DNA viruses having a double-stranded, circular DNA genome of 7800 to 7900 base pairs, a nonenveloped virion and an icosahedral capsid made of 72 capsomers. The genome contains three major regions, one coding for late genes, one coding for early genes and a non-coding region (Park et al., *Cancer* 76-1902-1913 (1995)). The non-coding region is also referred to as upstream regulatory region. This region is about 400 base pairs long and contains an array of binding sites for the various transcription factors controlling expression of early and late genes. The late gene region has two separate open reading frames encoding viral capsid proteins L1 and L2. Protein L1 is the major capsid protein that is highly conserved among different HPV species. The early gene region includes six open reading frames, designated E1, E2, E4, E5, E6 and E7. Proteins E6 and E7 are oncoproteins critical for viral replication as well as for host cell immortalization and transformation. Proteins E1, E2 and E4 also play an important role in virus replication. In addition, E4 functions in the maturation of the virus. The role of E5 is less well known.

Cells from malignant tumors share two important growth characteristics. They are immortalized, i.e., they do not senesce, and they are capable of anchorage-independent growth. Introduction of HPV 16 or HPV 18 DNA into immortalized rodent cells results in their transformation, i.e., they acquire the ability to grow in the absence of substratum attachment and the capacity to form tumors when injected into mice (Crook et al., *Proc. Natl. Acad. Sci. USA* 85:8820-24 (1988)). A different result is obtained when HPV DNAs are introduced into early passage, non-immortalized cells: the cells become immortalized but are not transformed (Woodworth et al., *Cancer Res.* 48:4620-28 (1988)). Thus, one pathway by which tumors develop involves a change that results in immortalization of cells followed by expression of HPV genes that results in their transformation. The HPV genes involved in transformation of cells in vitro are those encoding E6 and/or E7 (Bedell et al., *J Virol* 61:3635-40 (1987)). Mechanisms by which the E6 and E7 proteins may cause cellular transformation have been proposed (Park et al., *Cancer* 76:1902-1913 (1995), and references cited therein).

E6 is a small (approximately 15,000 MW) polypeptide containing Zn-binding domains. A clue to its transforming function was provided by the observation that the protein binds p53. The p53 protein is a well known tumor suppressor protein that negatively regulates cell cycle progression and, consequently, cell growth and division. Binding of E6 to p53 results in the ubiquination and eventual degradation of the latter protein, which process involves another cellular protein termed "E6-associated protein". Consequently, cells expressing E6 will have a reduced basal level of p53. p53 levels are elevated in response to DNA damage. Such increased levels result in the enhanced expression of p21, an inhibitor of cyclin-dependent kinases, which protein mediates cell cycle arrest. This mechanism provides cells with a time window within which they can repair damaged DNA prior to its replication, which would result in the establishment of the damage/mutation. E6-mediated enhanced turnover of p53 may prevent the mechanism from operating. Recently, it was also found that E6 not only affects cell cycle regulation by virtue of accelerating degradation of p53, but also, more directly, by blocking p53 from interacting with DNA (Thomas et al., *Oncogene* 10:261-8 (1995)).

The E7 protein is a small (approximately 10,000 Mw), Zn-binding phosphoprotein capable of binding the retinoblastoma gene product Rb. Rb is a tumor suppressor binding to and inactivating transcription factor E2F. The latter factor controls transcription of a number of growth-related genes including those encoding thymidine kinase, c-myc, dihydrofolate reductase and DNA polymerase alpha. Rb-E2F complex formation prevents the expression of the latter genes in G0 and G1 phases, restricting their expression to the S phase where the Rb-E2F complexes are programmed to dissociate, liberating active transcription factor E2F. Formation of Rb-E7 complexes prevents formation of Rb-E2F complexes with the result of shortening pre-S phases, i.e., accelerating progression through the cell cycle. Correlative evidence for the importance of these mechanisms is provided by the observations that E6 proteins from highly oncogenic HPV types (e.g., HPV 16 & 18) have higher affinities for p53 than corresponding proteins from non-oncogenic types, and that E7 proteins from highly oncogenic types have higher affinities for Rb than corresponding proteins from non-oncogenic types.

In a majority of cervical cancers and precursor lesions, HPV DNA is integrated in the host cell genome (Cullen et al., *J. Virol.* 65:606-12 (1991)). It appears that in most cases, integration involves breakage of the HPV genomic DNA in the E1/E2 region, leaving the E6/E7 region intact. A consequence of the breakage in the E1/E2 region is an interruption of the open reading frame encoding two different E2 proteins, the smaller of which proteins functions as a transcriptional repressor of early gene expression. This leads to an upregulation of E6 and E7 expression.

SUMMARY OF THE INVENTION

The present invention relates to compositions for inducing an immune response against an HPV protein antigen in a subject to which they are administered. The immune response can be a humoral or cellular response, in particular, a cell-mediated, cytolytic response to an HPV protein antigen. The compositions can be used prophylactically or therapeutically. In a prophylactic application, induction of an immune response refers to elicitation of immune reactions over a very low background of inherent immunity. In a therapeutic application, induction of an immune response in a subject refers to the generation of responses that exceed, either in magnitude or in quality, responses previously elicited by contact with HPV protein antigens exhibited either by the virus or by infected or transformed cells of the subject. In particular embodiments, the compositions are used to generate immune responses to tumor cells expressing and exhibiting an HPV protein antigen. In these embodiments, preferred HPV protein antigens targeted by the compositions are the E6 and E7 early viral proteins that are known to be consistently expressed in HPV-associated tumors. In one embodiment, the compositions comprise an HPV protein antigen joined to a stress protein (or heat shock protein (Hsp)). The HPV protein antigen may be joined to the stress protein by chemical conjugation, or antigen and stress protein may be joined at the nucleotide level permitting expression and isolation of a fusion protein containing both antigen and stress protein sequences. The compositions can be introduced into a subject or used ex vivo to stimulate and/or cause expansion of a subject's immune cells targeting or mediating targeting of HPV or cells including tumor cells exhibiting an HPV protein antigen. The compositions are effective in stimulating an immune response when administered as nonparticulate (e.g., not as part of a virus or virus-like particle) proteinaceous solutions in the absence of adjuvant.

In another embodiment, the compositions comprise an expression vector including nucleic acid sequences encoding an HPV protein antigen and a stress protein. The expression vector further comprises sequence elements directing transcription and translation of the coding sequences and may also include elements facilitating delivery to and persistence or amplification of nucleic acids in cells of a subject. The expression vector can be introduced into cells of a subject, or it can be used to transduce a subject's cells ex vivo, resulting in the expression of an HPV protein antigen-stress protein fusion protein that will induce an immune response against the HPV protein antigen.

The present invention also relates to compositions comprising an HPV protein antigen joined to a stress protein in combination with another pharmacologically acceptable component. In one embodiment, the composition comprises a conjugate comprising a stress protein joined with an HPV protein antigen. In another embodiment, the composition comprises a fusion protein (e.g., proteins expressed from pET65HE6 and pET65HE7) in which a stress protein is fused to an HPV protein antigen. The conjugates and fusion proteins of these compositions are also claimed as are expression vectors encoding and capable of directing the expression of a fusion protein comprising a stress protein and an HPV protein antigen sequence in a subject's cells.

The present invention also relates to uses of the compositions to enhance immune responses against HPV protein antigens and, in particular embodiments, against tumors exhibiting an HPV protein antigen. The articles from the scientific literature and patent applications cited herein, especially those relating to the preparation and use of compositions of the invention, are incorporated by reference in their entirety.

DETAILED DESCRIPTION OF THE INVENTION

Figure 1:
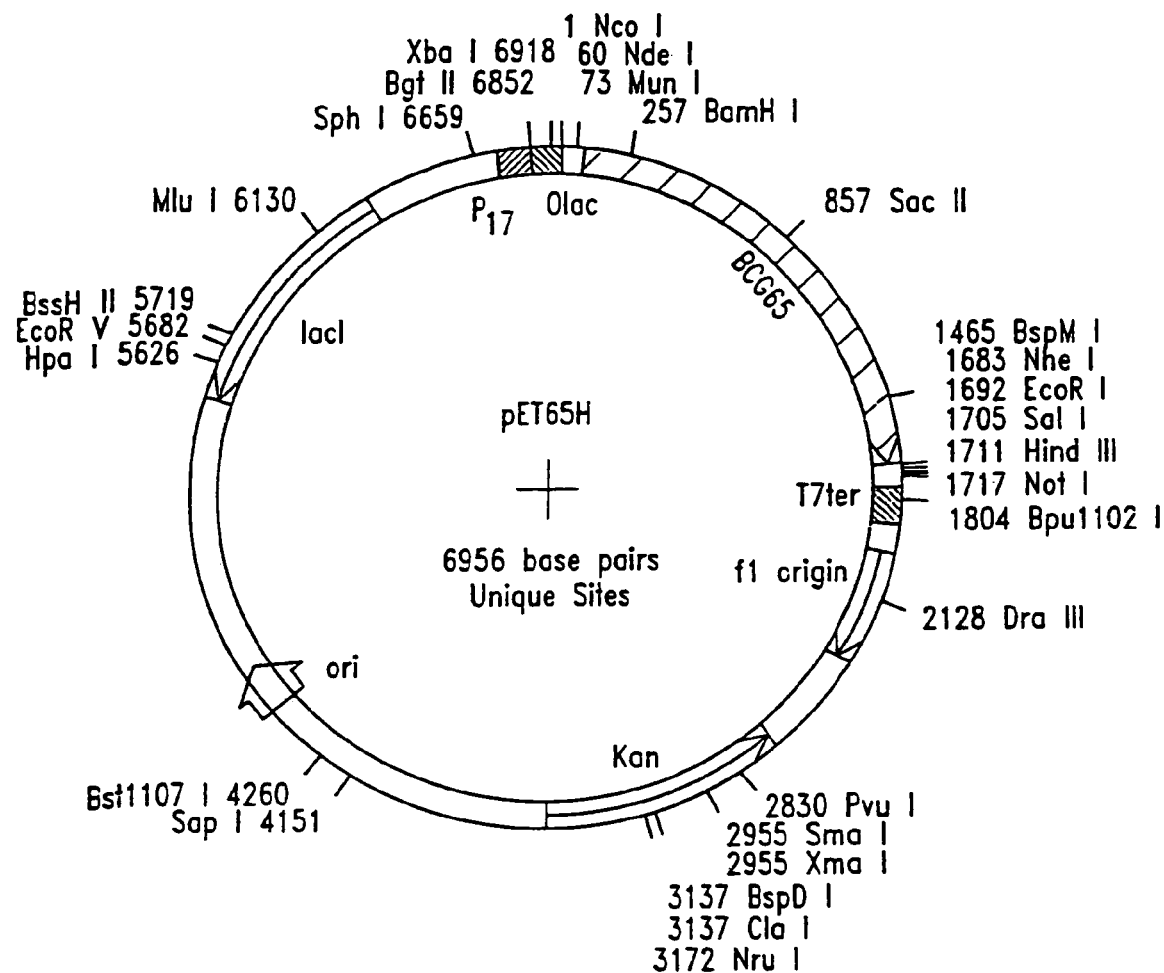
FIG. 1 is a schematic representation of construct pET65H.

The present invention relates to compositions that induce an immune response in a subject to human papillomavirus of cells of the subject exhibiting a protein antigen of an HPV. In one embodiment, the compositions comprise an HPV protein antigen and a stress protein. In another embodiment, the compositions comprise an expression vector capable of directing the expression of an HPV protein antigen-stress protein fusion protein.

The compositions of the present invention can be used prophylactically to raise immunity against an HPV protein antigen, preventing the establishment and proliferation of HPV or of cells of a subject expressing and exhibiting the HPV protein antigen or presenting portions thereof. The compositions can also be used therapeutically in a subject previously infected with an HPV to prevent further viral proliferation or to eliminate cells of the subject that proliferate as a consequence of HPV infection, including tumors expressing and exhibiting an HPV antigen or presenting a portion of the antigen. When reference is made herein to an HPV protein antigen as a target of an immune response induced by a composition of the present invention, the HPV protein antigen is understood to include an entire HPV protein or a polypeptide (molecular weight greater than 10 kDa) portion of the HPV protein exhibited on the surface of HPV or an infected cell of a subject as well as peptide displayed by an infected cell as a result of processing and presentation of the HPV protein, for example, through the typical MHC class I or II pathways.

The genomic sequences of many different types of HPV were cloned and were characterized by DNA sequence analysis. Bacterial vectors containing complete or partial HPV genomes are available from various sources including, for example, the American Tissue Culture Collection (ATCC). Additional types of HPV useful for the practice of the present invention can be isolated and typed by the methods previously established for this purpose, which methods are well known in the art.

HPV expresses six or seven non-structural and two structural proteins, and each of these proteins could, in principle, serve as a target for immunoprophylactic or immunotherapeutic approaches aimed at eliminating HPV and/or infected cells. Viral capsid proteins L1 and L2 are the structural proteins of HPV which are encoded by late genes. L1 is the major capsid protein that is highly conserved among different HPV species. The seven non-structural proteins are products of the early viral genes. Proteins E1, E2 and E4 play an important role in virus replication. Protein E4 functions additionally in the maturation of the virus. The role of E5 is less well known. Proteins E6 and E7 are oncoproteins critical for viral replication as well as for host cell immortalization and transformation. These proteins, that can be incorporated in the compositions of the present invention, are referred to as HPV protein antigens.

Of particular importance in the application of the present invention to the prophylactic and therapeutic treatment of HPV-associated cancers is the observation that HPV E6 and E7 proteins are consistently expressed in cervical cancers (Zur Hausen, *Appl. Pathol.* 5:19-24 (1987); Pater and Pater, *Virology* 145:313-8 (1985)). Kinoshita et al., *Br. J. Cancer* 71:344-9 (1995)) have demonstrated that the E6 and E7 genes are also expressed in lung carcinoma. Moreover, some natural immune (humoral) immune response to E7 was noted in cervical cancer patients (Jochmus-Kudielka et al., *J Nat'l Cancer Inst.* 81:1698-704 (1989)). Finally, model studies demonstrate that immunization with a modified E7 protein protects mice against a challenge with lung cells transformed with an activated c-Ha-ras gene and HPV E6/E7 genes (Lin et al., *Cancer Res.* 56:21-26 (1996)). From the points of view that these proteins are typically expressed in cancers arising as a consequence of HPV infection, that the same proteins are also the oncogenes which most likely played a major role in the development and maintenance of the cancers, and that an immune response can be directed against these proteins, E6 and E7 are preferred targets for immunintervention or prophylaxis, and, hence, are preferred HPV protein antigens of compositions of the present invention to be-used to prevent or treat HPV-associated cancer.

It has been shown in several animal models that cytotoxic T cell (CTL) peptides can induce protective immunity against certain viruses (Kast and Melief, *Immunol. Lett.* 30:229 (1991)). It has been observed that immunosuppressed individuals more often develop cervical carcinoma than immunocompetent individuals (Schneider et al., *Acta Cytologica* 27:220-4 (1983)). This strongly suggests that the cellular arm of the immune system, particularly the T cell system, are of major importance in the immunological defense against HPV-associated malignancy. Supporting evidence for the importance of a CTL response in producing protective immunity against E6- and E7-transformed cells came from an experiment in which mice vaccinated with a relevant CTL epitope of HPV 16 E7 were protected against transplantable HPV 16-induced tumors (Feltkamp et al., *Eur. J. Immunol.* 23:2242 (1993)). The present invention is based on our observation that linkage of a stress protein to an HPV protein antigen results in a composition that strongly stimulates cellular, in particular cell-mediated cytolytic, responses against the linked HPV protein antigen, which responses can kill cells exhibiting the HPV antigen.

An HPV protein antigen of the present invention can be any HPV-encoded polypeptide. In addition, it can be a portion of an HPV protein, provided that the portion, when joined with a stress protein, retains the ability to induce an immune response against the HPV protein antigen exhibited by infected cells or displayed by HPV. Compositions of the invention comprising various portions of an HPV antigen rather than a complete HPV protein antigen can be produced by routine methods such as those described hereinafter or in molecular biology and biochemistry textbooks. Sambrook et al., *Molecular Cloning: A Laboratory Manual*, 2d Ed., Cold Spring Harbor Laboratory Press (1989); Deutscher, M., *Guide to Protein Purification Methods Enzymology*, vol. 182, Academic Press, Inc., San Diego, Calif. (1990). Each composition having a particular portion of an HPV protein antigen can be tested for the degree and quality of the immune response against the HPV protein antigen in experiments such as those described in the examples described hereinafter. Minimally, an HPV protein antigen in a composition of the present invention will contain at least one B or T cell epitope (e.g., a CTL or a T helper cell epitope) of an HPV protein. When reference is made to compositions of the present invention, the term "HPV protein antigen" includes portions of an HPV protein antigen, provided that such portions retain the ability to induce an immune response against the HPV protein antigen exhibited by infected cells or displayed by HPV.

E6 and particularly E7 are transforming proteins. In compositions including as the HPV protein antigen a complete HPV E6 or E7 protein sequence or a portion sufficiently complete to retain transforming ability, the transforming nature of the antigen may or may not represent a substantial risk, depending on the method by which the HPV antigen is manufactured. For example, in cases in which an HPV protein antigen or a composition including such antigen is prepared by recombinant techniques that carry a risk of DNA contamination, it may be prudent to undertake steps to eliminate the transforming ability of the antigen. When using compositions including an expression vector directing the expression in a subject of a fusion protein including a complete HPV E6 or E7 protein sequence or a portion sufficiently complete to retain transforming ability, it may be necessary to eliminate sequences that render the protein product transforming. Nontransforming variants of E6 and E7 were obtained by fusing E6 and E7 sequences (PCT/AU95/00868). It is therefore possible that certain fusion proteins including E6 or E7 sequences and stress protein sequences may already be nontransforming. Alternatively, sequences may be selectively deleted from E6 or E7 using techniques that are well known in the art, and that have also been described in PCT/AU95/00868. The deletions can be made in expression vectors expressing E6 or E7 sequences alone or in vectors expressing E6- or E7-stress protein fusion proteins. The results of such manipulations can be assessed by testing the transforming ability of deletion proteins in a transfection experiment. For example, NIH3T3 cells can be transfected with an expression vector including a gene for a deletion protein, and transforming ability can be estimated by colony-forming assay in soft agar. This particular test is also described in PCT/AU95/00868.

In one embodiment of the present invention, compositions are comprised of two moieties: a stress protein and a protein antigen of HPV against which a cellular immune response is desired. The two moieties are joined to form a single unit. The two moieties can be connected by conjugation, i.e., through a covalent bond between the stress protein and the HPV protein antigen. Hermanson, G. T., *Bioconjugate Techniques*, Academic Press, Inc., San Diego, Calif. (1996); Lussow, A. R. et al., *Eur. J. Immun.* 21:2297-2302 (1991); Barrios, C. et al., *Eur. J. Immun.* 22:1365-1372 (1992)). Alternatively, recombinant techniques can be used to connect and express the two moieties, which techniques result in a recombinant fusion protein which includes the stress protein and the HPV protein antigen in a single molecule. This makes it possible to produce and purify a single recombinant molecule in the production process. The two moieties can also be joined noncovalently. Any of several known high-affinity interactions can be adapted to, noncovalently connect the two moieties. For example, a biotin group can be added to an HPV protein antigen, and the stress protein to be joined can be expressed as an avidin—stress protein fusion protein. The avidin—stress protein fusion protein will strongly bind the biotinylated HPV protein antigen. Analogously, portions of HPV protein antigens can be joined to a complete stress protein or to portions of the stress protein, and portions of a stress protein can be joined to a complete HPV protein antigen or to portions of the HPV protein antigen, provided that the respective portions are sufficient to induce an immune response against the HPV protein antigen in a subject to whom it is administered. In another embodiment, compositions comprise an expression vector capable of directing the expression of an HPV protein antigen—stress protein fusion protein.

Any suitable stress protein (heat shock protein (hsp)) can be used in the compositions of the present invention. For example, as described in the examples, Hsp60 and/or Hsp70 can be used. Turning to stress proteins generally, cells respond to a stressor (typically heat shock treatment) by increasing the expression of a group of genes commonly referred to as stress, or heat shock, genes. Heat shock treatment involves exposure of cells or organisms to temperatures that are one to several degrees Celsius above the temperature to which the cells are adapted. In coordination with the induction of such genes, the levels of corresponding stress proteins increase in stressed cells. As used herein, a "stress protein," also known as a "heat shock protein" or "Hsp," is a protein that is encoded by a stress gene, and is therefore typically produced in significantly greater amounts upon the contact or exposure of the stressor to the organism. A "stress gene," also known as "heat shock gene" is used herein as a gene that is activated or otherwise detectably upregulated due to the contact or exposure of an organism (containing the gene) to a stressor, such as heat shock, hypoxia, glucose deprivation, heavy metal salts, inhibitors of energy metabolism and electron transport, and protein denaturants, or to certain benzoquinone ansamycins. Nover, L., *Heat Shock Response*, CRC Press, Inc., Boca Raton, Fla. (1991). "Stress gene" also includes homologous genes within known stress gene families, such as certain genes within the Hsp70 and Hsp90 stress gene families, even though such homologous genes are not themselves induced by a stressor. Each of the terms stress gene and stress protein as used in the present specification may be inclusive of the other, unless the context indicates otherwise.

In particular embodiments, e.g., in cases involving chemical conjugates between a stress protein and an HPV protein antigen, the stress proteins used in the present invention are isolated stress proteins, which means that the stress proteins have been selected and separated from the host cell in which they were produced. Such isolation can be carried out as described herein and using routine methods of protein isolation known in the art. Maniatis et al., *Molecular Cloning, A Laboratory Manual*, Cold Spring Harbor Laboratory, Cold Spring Harbor, N.Y. (1982); Sambrook et al., *Molecu-* lar Cloning: A Laboratory Manual, 2d Ed., Cold Spring Harbor Laboratory Press (1989); Deutscher, M., Guide to Protein Purification Methods Enzymology, vol. 182, Academic Press, Inc., San Diego, Calif. (1990).

In bacteria, the predominant stress proteins are proteins with molecular sizes of about 70 and 60 kDa, respectively, that are commonly referred to as Hsp70 and Hsp60, respectively. These and other specific stress proteins and the genes encoding them are discussed further below. In bacteria, Hsp70 and Hsp60 typically represent about 1-3% of cell protein based on the staining pattern using sodium dodecyl sulfate polyacrylamide gel electrophoresis and the stain Coomassie blue, but accumulate to levels as high as 25% under stressful conditions. Stress proteins appear to participate in important cellular processes such as protein synthesis, intracellular trafficking, and assembly and disassembly of protein complexes. It appears that the increased amounts of stress proteins synthesized during stress serve primarily to minimize the consequences of induced protein unfolding. Indeed, the preexposure of cells to mildly stressful conditions that induce the synthesis of stress proteins affords protection to the cells from the deleterious effects of a subsequent more extreme stress.

The major stress proteins appear to be expressed in every organism and tissue type) examined so far. Also, it appears that stress proteins represent the most highly conserved group of proteins identified to date. For example, when stress proteins in widely diverse organisms are compared, Hsp90 and Hsp70 exhibit 50% or higher identity at the amino acid level and share many similarities at non-identical positions. It is noted that similar or higher levels of homology exist between different members of a particular stress protein family within species.

The genes encoding stress proteins may be present in a single copy or in multiple, non-identical copies in the genome of a cell or organism. For example, the human genome has been shown to contain at least one copy of an hsp100 gene, at least two different hsp90 genes, up to ten hsp70 genes of which at least several are non-identical copies, several T complex genes (Tcp genes) and at least one gene encoding the related mitochondrial protein Hsp60, as well as at least three copies of small hsp genes encoding Hsps in the 20-30 kDa range of molecular size. In most families of stress genes there is at least one gene whose expression level is relatively high and is either entirely constitutive or only mildly heat shock-inducible. Furthermore, several families of stress genes include members that are not up-regulated by heat but by other cues such as increased calcium levels, etc.

The stress proteins, particularly Hsp70, Hsp60, Hsp20-30 and Hsp10, are among the major determinants recognized by the host immune system in the immune response to infection by *Mycobacterium tuberculosis* and *Mycobacterium leprae*. Young, R. A. and Elliott, T. J., Stress Proteins, Infection, And Immune Surveillance, Cell 50:5-8 (1989). Further, some rat arthritogenic T cells recognize Hsp60 epitopes. Van Eden, W. et al., Nature 331:171-173 (1988). However, individuals, including healthy individuals, with no history of mycobacterial infection or autoimmune disease also carry T cells that recognize both bacterial and human Hsp60 epitopes; a considerable fraction of T cells in healthy individuals that are characterized by expression of the gamma-delta T cell receptor recognize both self and foreign stress proteins. O'Brien, R. et al., Cell 57:664-674 (1989). Thus, individuals, even healthy individuals possess T-cell populations that recognize both foreign and self stress protein epitopes.

This system recognizing stress protein epitopes presumably constitutes an "early defense system" against invading organisms. Murray, P. J. and Young, R. A., J. Bacteriol 174: 4193-6 (1992). The system may be maintained by frequent stimulation by bacteria and viruses. As discussed before, healthy individuals have T cell populations recognizing self stress proteins. Thus, the presence of autoreactive T cells is compatible with normal health and does not cause autoimmune disease; this demonstrates the safety of stress proteins within an individual. The safety of stress proteins is additionally demonstrated by the success and relative safety of BCG (*Bacille Calmette* Guerin, a strain of *Mycobacterium bovis*) vaccinations, which induce an immune response against stress proteins that is also protective against *Mycobacterium tuberculosis*.

Families of stress genes and proteins for use in the present invention are those well known in the art and include, for example, Hsp100-200, Hsp100, Hsp90, Lon, Hsp70, Hsp60, TF55, Hsp40, FKBPs, cyclophilins, Hsp20-30, ClpP, GrpE, Hsp10, ubiquitin, calnexin, and protein disulfide isomerases. Macario, A. J. L., Cold Spring Harbor Laboratory Res. 25:59-70, 1995; Parsell, D. A. & Lindquist, S. Ann. Rev. Genet. 27:437-496 (1993); U.S. Pat. No. 5,232,833 (Sanders et al.). A particular group of stress proteins includes Hsp90, Hsp70, Hsp60, Hsp20-30, further preferably Hsp70 and Hsp60.

Hsp100-200 examples include Grp170 (for glucose-regulated protein). Grp170 resides in the lumen of the ER, in the pre-golgi compartment, and may play a role in immunoglobulin folding and assembly.

Hsp100 examples include mammalian Hsp 110, yeast Hsp104, ClpA, ClpB, ClpC, ClpX and ClpY. Yeast Hsp104 and *E. coli* ClpA, form hexameric and *E. coli* ClpB, tetrameric particles whose assembly appears to require adenine nucleotide binding. Clp protease provides a 750 kDa heterooligomer composed of ClpP (a proteolytic subunit) and of ClpA. ClpB-Y are structurally related to ClpA, although unlike ClpA they do not appear to complex with ClpP.

Hsp90 examples include HtpG in *E. coli*, Hsp83 and Hsc83 yeast, and Hsp90alpha, Hsp90beta and Grp94 in humans. Hsp90 binds groups of proteins, which proteins are typically cellular regulatory molecules such as steroid hormone receptors (eg., glucocorticoid, estrogen, progesterone, and testosterone receptors), transcription factors and protein kinases that play a role in signal transduction mechanisms. Hsp90 proteins also participate in the formation of large, abundant protein complexes that include other stress proteins.

Lon is a tetrameric protein functioning as an ATP-dependent protease degrading non-native proteins in *E. coli*.

Hsp70 examples include Hsp72 and Hsc73 from mammalian cells, DnaK from bacteria, particularly mycobacteria such as *Mycobacterium leprae, Mycobacterium tuberculosis*, and *Mycobacterium bovis* (such as Bacille-Calmette Guerin; referred to herein as Hsp71), DnaK from *Escherichia coli*, yeast, and other prokaryotes, and BiP and Grp78. Hsp70 is capable of specifically binding ATP as well as unfolded polypeptides and peptides, thereby participating in protein folding and unfolding as well as in the assembly and disassembly of protein complexes.

Hsp60 examples include Hsp65 from mycobacteria. Bacterial Hsp60 is also commonly known as GroEL, such as the GroEL from *E. coli*. Hsp60 forms large homooligomeric complexes, and appears to play a key role in protein folding. Hsp60 homologues are present in eukaryotic mitochondria and chloroplasts.

TF55 examples include Tcpl, TRiC and thermosome. The proteins typically occur in the cytoplasm of eukaryotes and some *archaebacteria*, and form multi-membered rings, promoting protein folding. They are also weakly homologous to Hsp60.

Hsp40 examples include DnaJ from prokaryotes such as *E. coli* and mycobacteria and HSJ1, HDJ1 and Hsp40. Hsp40 plays a role as a molecular chaperone in protein folding, thermotolerance and DNA replication, among other cellular activities.

FKBPs examples include FKBP12, FKBP13, FKBP25, and FKBP59, Fprl and Nepl. The proteins typically have peptidyl-prolyl isomerase activity and interact with immunosuppressants such as FK506 and rapamycin. The proteins are typically found in the cytoplasm and the endoplasmic reticululum.

Cyclophilin examples include cyclophilins A, B and C. The proteins have peptidyl-prolyl isomerase activity and interact with the immunosuppressant cyclosporin A. The protein cyclosporin A binds calcineurin (a protein phosphatase).

Hsp20-30 is also referred to as small Hsp. Hsp20-30 is typically found in large homooligomeric complexes or, possibly, also heterooligomeric complexes where an organism or cell type expresses several different types of small Hsps. Hsp20-30 interacts with cytoskeletal structures, and may play a regulatory role in the polymerization/depolymerization of actin. Hsp20-30 is rapidly phosphorylated upon stress or exposure of resting cells to growth factors. Hsp20-30 homologues include alpha-crystallin.

ClpP is an *E. coli* protease involved in degradation of abnormal proteins. Homologues of ClpP are found in chloroplasts. ClpP forms a heterooligomeric complex with ClpA.

GrpE is an *E. coli* protein of about 20 kDa that is involved in both the rescue of stress-damaged proteins as well as the degradation of damaged proteins. GrpE plays a role in the regulation of stress gene expression in *E. coli*.

Hsp10 examples include GroES and Cpn10. Hsp10 is typically found in *E. coli* and in mitochondria and chloroplasts of eukaryotic cells. Hsp10 forms a seven-membered ring that associates with Hsp60 oligomers. Hsp10 is also involved in protein folding.

Ubiquitin has been found to bind proteins in coordination with the proteolytic removal of the proteins by ATP-dependent cytosolic proteases.

In particular embodiments, the stress proteins of the present invention are obtained from *enterobacteria*, mycobacteria (particularly *M. leprae, M. tuberculosis, M. vaccae, M. smegmatis* and *M. bovis*), *E. coli*, yeast, *Drosophila*, vertebrates, avians, chickens, mammals, rats, mice, primates, or humans.

The stress proteins may be in the form of acidic or basic salts, or in neutral form. In addition, individual amino acid residues may be modified by oxidation or reduction. Furthermore, various substitutions, deletions, or additions may be made to the amino acid or nucleic acid sequences, the net effect of which is to retain or further enhance the increased biological activity of the stress protein. Due to code degeneracy, for example, there may be considerable variation in nucleotide sequences encoding the same amino acid sequence. The present invention is also suitable for use with portions of stress proteins or peptides obtained from stress proteins, provided such portions or peptides include the epitopes involved with enhancing the immune response to the chosen HPV protein antigen. Portions of stress proteins may be obtained by fragmentation using proteinases, or by recombinant methods, such as the expression of only part of a stress protein-encoding nucleotide sequence (either alone or fused with another protein-encoding nucleic acid sequence). Peptides may also be produced by such methods, or by chemical synthesis. The stress proteins may include mutations introduced at particular loci by a variety of known techniques. See, e.g., Sambrook et al., *Molecular Cloning: A Laboratory Manual*, 2d Ed., Cold Spring Harbor Laboratory Press (1989); Drinkwater and Klinedinst *Proc. Natl. Acad. Sci. USA* 83:3402-3406 (1986); Liao and Wise, *Gene* 88:107-111 (1990); Horwitz et al., *Genome* 3:112-117 (1989). The term stress protein as used herein is intended to include such portions and peptides of a stress protein.

Methods of identifying a gene or a protein under consideration as a stress gene or protein are well known in the art. For example, the conservation of the genes and proteins of a particular stress protein family permits comparison of the nucleotide or amino acid sequence of the gene/protein under consideration with well known stress genes such as DnaK, GroEL or DnaJ, e.g., by nucleic acid hybridization or nucleic acid or amino acid sequencing followed by computer comparison analysis. Voellmy, R., et al., *Proc. Nat'l Acad. Sci. USA* 82:4949-4953 (1985). Alternatively, an assay may be used to identify and/or discriminate between essential structural features and/or functional properties of a selected stress protein. For example, an expression library may be screened using anti-Hsp antibodies. Hsp90 is well known to bind the benzoquinone ansamycin geldanamycin with high affinity. An expression library could therefore be screened with geldanamycin to discover putative homologs of Hsp90 as proteins binding the benzoquinone ansamycin. The nature of the protein encoded by the isolated nucleic acid could be further confirmed by other assays including antibody-based assays. *Antibodies: A Laboratory Manual*, Harlow and Lane (eds.), Cold Spring Harbor Laboratory Press (1988). In addition, the biological activity of a given stress protein group may be exploited. Guidon, P. T., and Hightower, L. E., *Biochem.* 25:3231-3239 (1986). For example, Hsp70 is capable of specifically binding ATP as well as unfolded polypeptides and peptides in the assembly of protein complexes. Thus, mixing a protein under consideration with a sample comprising appropriate polypeptides, peptides, or ATP, followed by determination of the presence or absence of production of protein-protein or protein-nucleotide complexes indicates the apparent presence or absence of an Hsp70 protein or gene, which presence or absence can be confirmed utilizing other assays such as antibody-based assays.

The stress protein, stress protein portion, stress protein homologue and the protein antigen of HPV to which the stress protein is conjugated or joined noncovalently present in the composition can be produced or obtained using known techniques. For example, the stress protein and/or the antigen can be obtained (isolated) from a source in which it is known to occur, can be produced and harvested from cell cultures or, in the case of the antigen, can be obtained from infected cells, can be produced by cloning, if necessary, and expressing a gene encoding the desired stress protein or the antigen, or can be synthesized chemically. Furthermore, a nucleic acid sequence encoding the desired stress protein or the antigen can be synthesized chemically. A fusion protein including a stress protein and an HPV protein antigen can be produced by recombinant means. For example, a nucleic acid encoding the stress protein can be joined to either end of a nucleic acid sequence encoding the HPV protein antigen such that the two protein-coding sequences are sharing a common translational reading frame and can be expressed as a fusion protein including the HPV protein-antigen and the stress protein. The combined sequence is inserted into a suitable vector chosen based on the expression features desired and the nature of the host cell. In the examples provided hereinafter, the nucleic acid sequences are assembled in a vector suitable for protein expression in the bacterium E. coli. Following expression in the chosen host cell, fusion protein can be purified by routine biochemical separation techniques or by immunoaffinity methods using an antibody to one or the other part of the fusion protein. Alternatively, the selected vector can add a tag to the fusion protein sequence, e.g., an oligohistidine tag as described in the examples presented hereinafter, permitting expression of a tagged fusion protein that can be purified by affinity methods using an antibody or other material having an appropriately high affinity for the tag. Sambrook et al., Molecular Cloning: A Laboratory Manual, 2d Ed., Cold Spring Harbor Laboratory Press (1989); Deutscher, M., Guide to Protein Purification Methods Enzymology, vol. 182, Academic Press, Inc., San Diego, Calif. (1990). If a vector suitable for expression in mammalian cells is used, e.g., one of the vectors discussed below, the fusion protein can be expressed and purified from mammalian cells. Alternatively, the mammalian expression vector (including fusion protein-coding sequences) can be administered to a subject to direct expression of the fusion protein in the subject's cells. A nucleic acid encoding a fusion protein including a stress protein and an HPV protein antigen can also be produced chemically and then inserted into a suitable vector for fusion protein production and purification or administration to a subject. Finally, a fusion protein can also be prepared chemically.

The compositions comprising a stress protein and an HPV antigen described herein can be used to enhance an immune response, particularly a cell-mediated cytolytic response, against an HPV, or HPV-infected or transformed cell expressing an HPV antigen. Preferably, compositions will contain protein antigen sequences from the particular HPV type against whose proteins an immune response is to be elicited.

The compositions comprising a stress protein and an HPV antigen described herein can be administered to a subject in a variety of ways. The routes of administration include intradermal, transdermal (e.g., slow release polymers), intramuscular, intraperitoneal, intravenous, subcutaneous, oral, epidural and intranasal routes. Any other convenient route of administration can be used, for example, infusion or bolus injection, or absorption through epithelial or mucocutaneous linings. In addition, the compositions described herein can contain and be administered together with other pharmacologically acceptable components such as biologically active agents (e.g., adjuvants such as alum), surfactants (e.g., glycerides), excipients (e.g., lactose), carriers, diluents and vehicles. Furthermore, the compositions can be used ex vivo as a means of stimulating white blood cells obtained from a subject to elicit, expand and propagate HPV protein antigen-specific immune cells in vitro that are subsequently reintroduced into the subject.

Further, a stress protein —HPV protein antigen fusion protein can be administered by in vivo expression of a nucleic acid encoding such protein sequences into a human subject. Expression of such a nucleic acid can also be achieved ex vivo as a means of stimulating white blood cells obtained from a subject to elicit, expand and propagate HPV antigen-specific immune cells in vitro that are subsequently reintroduced into the subject. Expression vectors suitable for directing the expression of HPV protein antigen-stress protein fusions can be selected from the large variety of vectors currently used in the field. Preferred will be vectors that are capable of producing high levels of expression as well as are effective in transducing a gene of interest. For example, recombinant adenovirus vector pJM17 (All et al., Gene Therapy 1:367-84 (1994); Berkner K. L., Biotechniques 6:616-24 1988), second generation adenovirus vectors DE1/DE4 (Wang and Finer, Nature Medicine 2:714-6 (1996)), or adeno-associated viral vector AAV/Neo (Muro-Cacho et al., J. Immunotherapy 11:231-7 (1992)) can be used. Furthermore, recombinant retroviral vectors MFG (Jaffee et al., Cancer Res. 53:2221-6 (1993)) or LN, LNSX, LNCX, LXSN (Miller and Rosman, Biotechniques 7:980-9 (1989)) can be employed. Herpes simplex virus-based vectors such as pHSV1 (Geller et al., Proc. Nat'l Acad. Sci 87:8950-4 (1990) or vaccinia viral vectors such as MVA (Sutter and Moss, Proc. Nat'l Acad. Sci. 89:10847-51 (1992)) can serve as alternatives.

Frequently used specific expression units including promoter and 3' sequences are those found in plasmid cDNA3 (Invitrogen), plasmid AH5, pRC/CMV (Invitrogen), pCMU II (Paabo et al., EMBO J. 5:1921-1927 (1986)), pZip-Neo SV (Cepko et al., Cell 37:1053-1062 (1984)) and pSRa (DNAX, Palo Alto, Calif.). The introduction of genes into expression units and/or vectors can be accomplished using genetic engineering techniques, as described in manuals like Molecular Cloning and Current Protocols in Molecular Biology (Sambrook, J., et al., Molecular Cloning, Cold Spring Harbor Press (1989); Ausubel, F. M. et al., Current Protocols in Molecular Biology, Greene Publishing Associates and Wiley-Interscience (1989)). A resulting expressible nucleic acid can be introduced into cells of a human subject by any method capable of placing the nucleic acid into cells in an expressible form, for example as part of a viral vector such as described above, as naked plasmid or other DNA, or encapsidated in targeted liposomes or in erythrocyte ghosts (Friedman, T., Science, 244:1275-1281 (1989); Rabinovich, N. R. et al., Science, 265:1401-1404 (1994)). Methods of transduction include direct injection into tissues and tumors, liposomal transfection (Fraley et al., Nature 370:111-117 (1980)), receptor-mediated endocytosis (Zatloukal et al., Ann. N.Y. Acad. Sci. 660:136-153 (1992)), and particle bombardment-mediated gene transfer (Eisenbraun et al., DNA & Cell. Biol. 12:791-797 (1993)).

The amount of stress protein and HPV protein antigen (fused, conjugated or noncovalently joined as discussed before) in the compositions of the present invention is an amount which produces an effective immunostimulatory response in a subject. An effective amount is an amount such that when administered, it results in an induction of an immune response. In addition, the amount of stress protein and HPV protein antigen administered to the subject will vary depending on a variety of factors, including the HPV protein antigen and stress protein employed, the size, age, body weight, general health, sex, and diet of the subject as well as on its general immunological responsiveness. Adjustment and manipulation of established dose ranges are well within the ability of those skilled in the art. For example, the amount of stress protein and antigen can be from about 1 microgram to about 1 gram, preferably from about 100 microgram to about 1 gram, and from about 1 milligram to about 1 gram. An effective amount of a composition comprising an expression vector is an amount such that when administered, it induces an immune response against the HPV protein antigen which it encodes. Furthermore, the amount of expression vector administered to the subject will vary depending on a variety of factors, including the HPV protein antigen and stress protein expressed, the size, age, body weight, general health, sex, and diet of the subject as well as on its general immunological responsiveness. Additional factors that need to be considered are the route of application and the type of vector used. For example, when prophylactic or therapeutic treatment is carried out with a viral vector containing a nucleic acid encoding an HPV protein antigen—stress protein fusion protein, the effective amount will be in the range of $10^4$ to $10^{12}$ helper-free, replication-defective virus per kg body weight, preferably in the range of $10^5$ to $10^{11}$ virus per kg body weight and most preferably in the range of $10^6$ to $10^{10}$ virus per kg body weight.

The present invention is illustrated by the following examples, which are not intended to be limiting in any way.

EXAMPLES

Example 1

Isolation of Recombinant Stress Proteins

Recombinant Mycobacterial Hsp71.

Plasmid Y3111 contains an *M. tuberculosis* hsp71 gene functionally inserted between expression control sequences (Mehlert, A. and Young, D. B., *Mol. Microbiol.* 3:125-130 (1989)). *E. coli* strain CG2027 (obtained from C. Georgopoulos, University of Geneva, Switzerland) containing a truncated dnaK gene was transformed with plasmid Y3111 by standard procedures. (Maniatis et al., *Molecular Cloning, A Laboratory Manual*, Cold Spring Harbor Laboratory, Cold Spring Harbor, N.Y. (1982)).

Bacteria containing plasmid Y3111 were grown overnight in 2×YT medium (20 g Tryptone, 10 g yeast extract, 10 g NaCl per liter) containing 100 microgram/ml ampicillin at 37° C., with agitation (250 rpm). A 10% glycerol stock was prepared from this culture and was stored at −70° C. Several scrapings from the frozen glycerol stock were used to inoculate a large culture that was incubated as before for about 48 h. When the optical density at 590 nm reached 2.5 to 3.5, cells were collected by centrifugation.

The following steps were performed at 4° C. Cell pellet was resuspended in 3 ml of lysis buffer per gram of pelleted cells. The composition of Lysis buffer was 10 mM Tris-HCl, 2 mM ethylenediamine tetraacetate (EDTA), 5 mM beta-mercaptoethanol, 10 microgram/ml aprotinin, 10 microgram/ml leupeptin, and 1 microgram/ml pepstatin. Lysozyme was added to the cell suspension to a final concentration of 0.14 mg/ml. The suspension was then frozen at −70° C.

The cell suspension was thawed, and cells were broken by sonication. Sonicate was subjected to centrifugation at 17,000 rpm for 30 min (JA-17 rotor, Beckmann). Solid $(NH_4)_2SO_4$ was added to the supernatant solution until that solution was 65% saturated with $(NH_4)_2SO_4$. After a 30 min incubation, the mixture was centrifuged as before. The pellet was dissolved in Q SEPHAROSE buffer A. To this solution were added 10 microgram/ml aprotinin, 10 microgram/ml leupeptin, and 1 microgram/ml pepstatin, and the solution was dialyzed overnight against 65 volumes of Q SEPHAROSE buffer A. Q SEPHAROSE buffer A contained 30 mM Tris-HCl (pH 7.5), 1 mM EDTA, 5 mM beta-mercaptoethanol. The dialyzed solution was clarified by centrifugation as described before.

Dialyzed solution was applied to a Q SEPHAROSE column (Pharmacia) equilibrated in Q SEPHAROSE buffer A. The column was washed with 2 volumes of the same buffer. Elution was with a 0 to 600 mM NaCl gradient. Fractions were tested by SDS-PAGE and staining with Coomassie Blue for the presence of a major 71 kDa polypeptide (i.e., the recombinant *M. tuberculosis* Hsp71 protein). Fractions containing the polypeptide were pooled, and the pool was brought to 65% saturation by the addition of solid $(NH_4)_2SO_4$. The mixture was centrifuged as described before, the pellet was dissolved in ATP Start buffer (50 mM Tris-HCl (pH 8.0), 20 mM NaCl, 5 mM $MgCl_2$, 15 mM beta-mercaptoethanol, 0.1 mM EDTA), and the resulting protein solution dialyzed overnight against 65 volumes of the same buffer and clarified by centrifugation.

The dialyzed protein solution was then applied to an ATP-agarose column (Fluka) equilibrated in ATP Start buffer. The column was washed with 1 column volume of ATP Start buffer with 1 M NaCl. Elution was achieved with ATP Start buffer supplemented with 10 mM ATP. The eluate was brought to 65% saturation with $(NH_4)_2SO_4$, and precipitated protein was collected as described before. The centrifugation pellet was dissolved in and dialyzed against 200 volumes of Blue SEPHAROSE buffer (30 mM Tris-HCl (pH 7.5), 5 mM $MgCl_2$, 5 mM beta-mercaptoethanol).

The dialyzed protein solution from the last step was applied to a Blue SEPHAROSE column (Pharmacia) equilibrated with Blue SEPHAROSE buffer. The column was washed with 1.5 column volumes of the same buffer. The flow-through and wash fractions (containing Hsp71) were collected as a single pool. The purity of the final preparation was assessed by SDS-PAGE and Coomassie Blue staining, by western blot analysis (Maniatis et al., *Molecular Cloning, A Laboratory manual*, Cold Spring Harbor Laboratory, Cold Spring Harbor, N.Y. (1982)); (see Sambrook et al., *Molecular Cloning: A Laboratory manual,* 2d. ed., Cold Spring Harbor Laboratory press, NY (1989)) using mouse monoclonal antibodies specific for mycobacterial Hsp71 and *E. coli* DnaK, respectively, and by assays of ATPase activity. Preparations are typically more than 90% pure based on the staining pattern of the preparation in Coomassie blue-stained gels, and preferably more than 95% pure, and contain less than 1% of *E. coli* GroEL and no detectable *E. coli* DnaK.

Recombinant Mycobacterial Hsp65

Plasmid RIB 1300 contains an *M. bovis* BCG hsp65 gene functionally inserted between expression control sequences. (Thole, J. E. R. et al., *J. Exp. Med.* 178:343-8 (1993). *E. coli* strain M1546 was transformed with plasmid RIB1300 (Thole, J. E. R., supra) using standard procedures. Maniatis et al., *Molecular Cloning, A Laboratory Manual*, Cold Spring Harbor Laboratory, Cold Spring Harbor, N.Y. (1982).

An inoculum of bacteria containing plasmid RIB 1300 was grown to saturation in NCZYM medium (10 g N-Z Amine A, 5 g Bacto yeast extract, 1 g Casamino acids, 5 g NaCl, 2 g $(NH_4)_2SO_4 \cdot 7H_2O$ per liter) containing 200 microgram/ml of ampicillin at 28° C. and under agitation (250 rpm). This culture was used to inoculate a larger culture which was grown under the same conditions as the inoculum culture until the optical density at 590 nm of the culture was between 0.3 and 0.6. Production of the recombinant protein was initiated by rapidly raising the temperature of the culture to 42° C. by incubation in a hot water bath. The culture was maintained at this temperature for 3 h with agitation. The bacteria were then collected by centrifugation and resuspended in 6 volumes per weight of bacterial pellet of lysis buffer. Lysis buffer contained 10 mM Tris-HCl (pH 8.0), 10 mM ethylediamine tetreacetate (EDTA), 0.1 mM PMSF and 0.1% RIVM BA (0.104 g 4-amino-benzamidine-2HCl, 0.066 g epsilon-amino caproic acid per 50 ml).

Lysozyme was added to a concentration of 0.1 mg/ml, and the suspension was frozen at −70° C.

The bacterial suspension was thawed and placed at 4° C. The following operations were at this temperature. Complete lysis of bacteria was achieved by sonication. The sonicate was centrifuged at 17,000 rpm for 30 min in a JA-17 rotor (Beckman). Saturated $(NH_4)_2SO_4$ was added to the supernatant solution until 20% saturation was achieved. Precipitates were removed by centrifugation (see above) and were discarded. The supernatant solution was brought to 55% saturation by the addition of saturated $(NH_4)_2SO_4$. The pellet resulting from the subsequent centrifugation was dissolved in TE buffer (10 mM Tris-HCl (pH 8.0), 15 mM beta-mercaptoethanol, 1 mM EDTA). The protein solution in TE was then dialyzed against 50 volumes of TE buffer.

After centrifugation (as above) to remove precipitated material, the dialyzed protein solution was applied to a DEAE SEPHAROSE (Pharmacia) column. After washing with TE buffer, proteins were eluted with a 0-300 mM NaCl gradient in TE buffer. Fractions containing M. bovis BCG Hsp65 were identified by SDS-PAGE and Coomassie blue staining and were pooled. 10 microgram/ml aprotinin, 10 microgram/ml leupeptin, and 1 microgram/ml pepstatin were added to the pool which was then concentrated in an Amicon cell using a YM30 membrane.

The concentrated pool was applied to a S-200 SEPHACRYL (Pharmacia) column equilibrated with S200 buffer (10 mM $Na_2HPO_4$ (pH 6.8), 150 mM NaC 1 and 15 mM beta-mercaptoethanol). Elution was with the same buffer. Fractions were tested for the presence of mycobacterial Hsp65 as before, and positive fractions containing highly purified protein were pooled and dialyzed overnight against HAP buffer (10 mM $Na_2HPO_4$ (pH 6.8), 15 mM beta-mercaptoethanol).

The dialyzed pool was applied to a hydroxyapatite (Bio-Rad; Bio-Gel HTP Gel) column equilibrated in HAP buffer. The column was washed with 3 column volumes of 1 mM $MgCl_2$ and 15 mM beta-mercaptoethanol and then with 1 mM $Na_2HPO_4$ (pH 6.8) and 15 mM beta-mercaptoethanol. Protein was eluted with a 10-60 mM phosphate gradient. Fractions were tested as before, and positive fractions were pooled, concentrated and exchanged into 0.85% NaCl by means of gel filtration through PD10 (Pharmacia). The purity of mycobacterial Hsp65 was assessed by SDS-PAGE and Coomassie blue staining as well as by western blot analysis using antibodies specific for *E. coli* DnaK and GroEL. Preparations were typically more than 90% pure, and contained no more than 0.5% of *E. coli* GroEL and 0.1-0.2% *E. coli* DnaK, respectively.

Hsp preparations can be depyrogenated either by affinity chromatography on DetoxiGel) resin (Pierce), addition of polymyxin B or by extraction with detergents such as Triton X-114 or X-100. Reduction in lipopolysaccharide content can be followed by the *limulus* amoebocyte assay (LAL; Biowhittaker, QCL 1000). Hsp preparations can be stored in buffer at −70° C., or can be kept, preferably at −70° C., as dried pellets after lyophilization.

Example 2

Preparation of Protein Antigen—Stress Protein Conjugates

This example is provided as an illustration of techniques that can be employed to prepare conjugates between a stress protein and a protein antigen, in this example a peptide derived from influenzavirus nucleoprotein (NP).

Synthesis of Stress Protein (Hsp71) and Antigen (NP.B)

*M. tuberculosis* Hsp71 was prepared as described in Example 1. NP peptide (referred to herein as NP.B; Motal, U. M. A. et al. *Eur. J. Immunol.* 25:11214 (1995) and references therein) with the amino acid sequence [C]VQLASNENMETM (SEQ ID NO: 1; the peptide contains an extra amino-terminal cysteine residue) corresponding to residues 363-374 in the complete NP and containing a known CTL epitope (H-2b-restricted) was produced synthetically (0.25 mM scale) on an Applied Biosystems model 431A peptide synthesizer using Fmoc (9-fluorenylmethyloxy-carbonyl) as the alpha-amino protective group and HMP (Wang) resin as the solid support. All amino acid and synthesis chemicals were purchased from Applied Biosystems. NP.B was cleaved off the support and side chain-protecting groups were removed by incubating under continuous agitation NP.B-resin for 3 hours in 2 ml of a mixture prepared by combining 10 ml trifluoroacetic acid, 0.5 ml water, 0.75 g crystalline phenol, 0.25 ml ethanedithiol and 0.5 ml thioanisole. The cleavage mixture was filtered into 40 ml of ice cold diethyl ether. Insoluble material was collected by centrifugation at 5000×g for 8 min. Ether was decanted and the pellet washed three times by resuspension in cold diethyl ether followed by centrifugation. After the last wash the pellet was air-dried, taken up in distilled water and lyophilized.

Chemical Conjugation of NP.B Peptide to Hsp71 and Diphtheria Toxoid

Conjugations were carried out with both Hsp71 and, to provide a standard for comparisons of efficacies of specific stimulation of CTL activity, commonly used carrier protein diphtheria toxoid (abbreviated DT; DT was obtained from Wako Chemical).

Activated carrier protein solutions: Nine mg of Hsp71 were dissolved in 4.5 ml of 0.1 M sodium borate buffer, pH 8.0. Sulfo-MBS (m-maleimidobenzoyl-N-hydroxy-sulfosuccinimide ester) (2.3 mg in 100 ul dimethyl sulfoxamine) was added to the protein, and the reaction mixture was incubated for 1 hour at room temperature. The pH was then adjusted to 6.0, and the reaction mixture dialyzed overnight at 4° C. against 1 liter of 20 mM sodium phosphate and 150 mM NaCl, pH 5.6. DT was similarly treated.

Reduced peptide solutions: For each conjugation reaction, 3 mg of peptide was dissolved in 100 ul of 0.1 M beta-mercaptoethanol. After 1 hour of incubation to allow reduction of the peptide, reducing agent was removed by drying the reaction mixture in a SpeedVac centrifuge. Peptide was redissolved in 0.5 ml distilled water to which 5 ul aliquots of 1 N NaOH were added until the peptide was fully dissolved. For conjugation experiments with DT, 6 mg of peptide were reduced and then redissolved in 1 ml of water.

The pH of the activated carrier protein solutions was adjusted to 6.8 using 0.1 N NaOH. Solution containing 3 mg of activated carrier protein was reacted with 0.5 ml of reduced peptide solution (or 1 ml of reduced peptide solution for the preparation of conjugates with DT) for 3 hours at room temperature with continuous mixing. To remove unreacted peptide, the resulting conjugate-containing solution was dialyzed overnight at 4° C. against 1 liter of 20 mM sodium phosphate and 150 mM NaCl, pH7. Protein concentration was determined by BCA assay. The efficiency of conjugation achieved by this procedure had been determined in prior pilot experiments using radiolabeled NP.B peptide. The peptide: protein ratio was found to be 17.5 for NP.B-Hsp71 conjugate (71.NP) and 10.1 for NP.B-DT (DT.NP).

Example 3

Preparation of Hsp-E6 and Hsp-E7 Fusion Genes

Preparation of Bacterial Expression Vector pET65H

Plasmid RIB 1300 contains a *Mycobacterium bovis* BCG hsp65 gene (Thole, J. E. R. et al. *J. Exp. Med.* 178:343-8 (1993)). A primer pair for amplification of the hsp65 gene was synthesized on an automated oligonucleotide synthesizer and was purified using routine procedures. The forward primer included an NdeI restriction site and had the nucleotide sequence 5'-AAT CAC TTC CAT ATG GCC AAG ACA ATT-3' (SEQ. ID NO:2). The reverse primer included EcoRI and NheI sites flanking a stop codon and had the nucleotide sequence 5'-CGC TCG GAC GAA TTC TCA GCT AGC GAA ATC CAT GCC-3' (SEQ. ID NO:3).

Polymerase chain reaction (PCR) was carried out using the above primer pair and pRIB 1300 as the DNA template. PCR fragments were double-digested with restriction endonucleases NdeI and EcoRI and ligated to NdeI/EcoRI-double-digested pET28a (Invitrogen) using routine subcloning procedures (Maniatis et al. *Molecular Cloning, A Laboratory Manual*, Cold Spring Harbor Lab., Cold Spring Harbor, N.Y. (1989)). Transformation-competent cells of *E. coli* strain DH5alpha were transformed with the ligation mixture and plated out on agar containing 100 ug/ml ampicillin. Colonies of transformed cells were isolated, and plasmid DNA prepared and analyzed for the presence of hsp65 gene and vector sequences by restriction mapping and nucleotide sequencing. Correct constructs (named pET65H) including the mycobacterial hsp65 gene were identified and were transformed into *E. coli* strain BL21(DE3; Novagen) for analysis of expression of the hsp65 gene. A schematic map of construct pET65H is shown in FIG. 1. To test for expression of Hsp65, transformed bacteria of strain BL21 were grown, induced and harvested using the manufacturer's instructions (Novagen). Bacteria were lysed, and soluble material as well as material solubilized from inclusion bodies by guanidinium hydrochloride (Maniatis et al. *Molecular Cloning, A Laboratory Manual*, Cold Spring Harbor Lab., Cold Spring Harbor, N.Y. (1989)) were electrophoresed on SDS-PAGE and subjected to anti-Hsp65 immunoblot using a monoclonal antibody specific for the mycobacterial stress protein.

Preparation of a Construct for Expression of an Hsp65-HPV16 E6 Fusion Protein in Bacteria A complete HPV16 E6-coding region was inserted at the carboxy-terminal end of the hsp65 gene in pET65H.

Plasmid pHPV16 contains a complete HPV16 genome in Bluescript vector SK(ATCC 45113). For the nucleotide sequence of the HPV16 genome, see Seedorf et al. *Virology* 145: 181-5 (1985). A primer pair for amplification of the E6 gene was synthesized on an automated oligonucleotide synthesizer and was purified using routine procedures. The forward primer included an NheI restriction site and had the nucleotide sequence 5'-AAA AGC AGA GCT AGC ATG CAC CAA AAG-3' (SEQ ID NO:4'). The reverse primer included EcoRI and a stop codon and had the nucleotide sequence 5'-CTC CAT GAA TTC TTA CAG CTG GGT-3' (SEQ ID NO:5).

Figure 2:
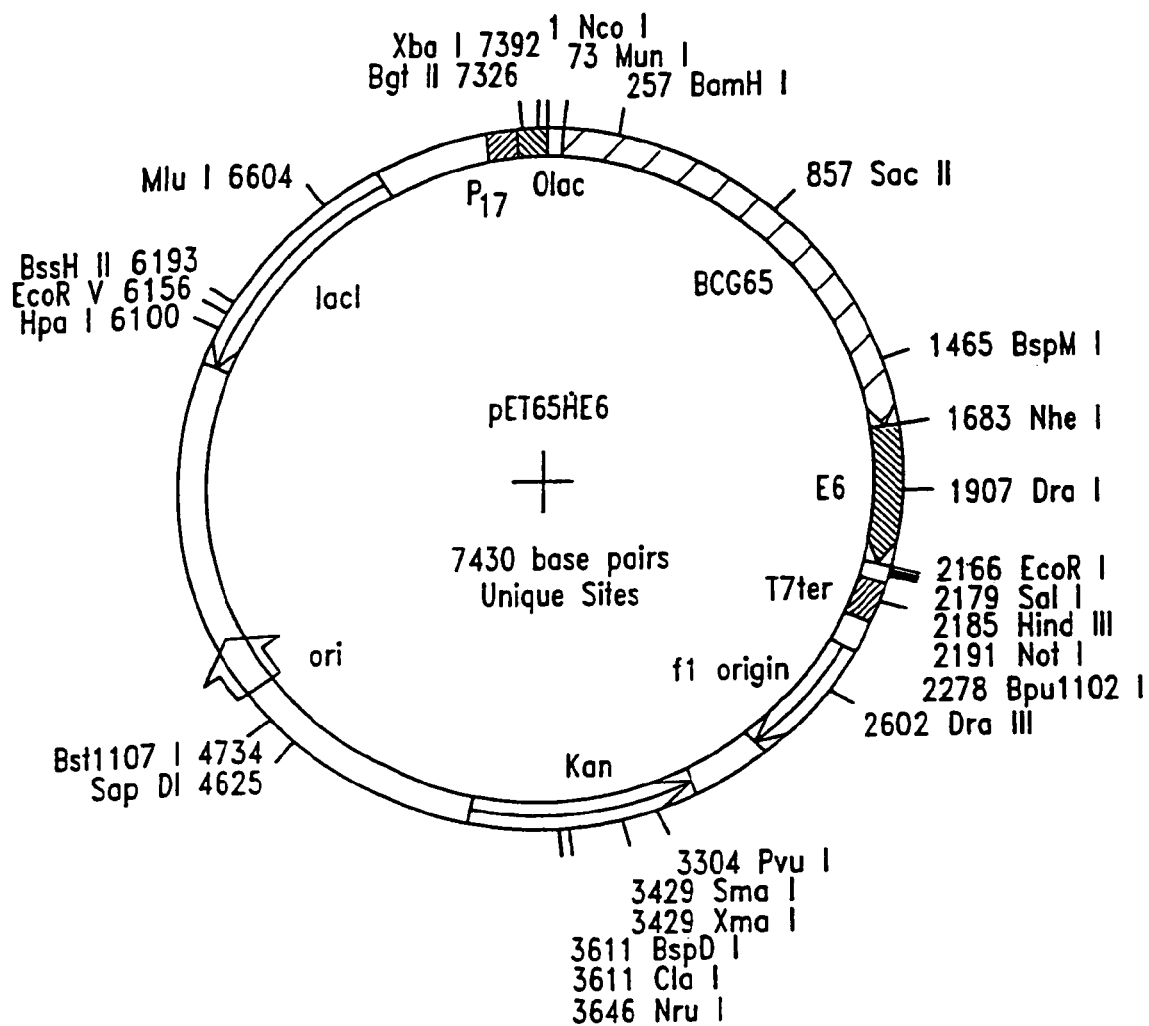
FIG. 2 is a schematic representation of construct pET65HE6.

Polymerase chain reaction (PCR) was carried out using the above primer pair and pHPV16 as the DNA template. PCR fragments were double-digested with restriction endonucleases NheI and EcoRI and ligated to NheI/EcoRI-double-digested pET65H using routine subcloning procedures (Maniatis et al., *Molecular Cloning, A Laboratory Manual*, Cold Spring Harbor Lab., Cold Spring Harbor, N.Y. (1989)). Transformation-competent cells of *E. coli* strain DH5alpha were transformed with the ligation mixture and plated out on agar containing 100 ug/ml ampicillin. Colonies of transformed cells were isolated, and plasmid DNA prepared and analyzed for the presence of hsp65-E6 fusion gene and vector sequences by restriction mapping and nucleic acid sequencing. Correct constructs (named pET65HE6) including the hsp65-E6 fusion gene were identified and were transformed into *E. coli* strain BL21(DE3; Novagen) for analysis of expression of the fusion gene. A schematic map of construct pET65HE6 is shown in FIG. 2. To test for expression of Hsp65-E6, bacteria of strain BL2 1 transformed with pET65HE6 were grown, induced and harvested using the manufacturer's instructions (Novagen). Bacteria were lysed, and soluble material as well as material solubilized from inclusion bodies by guanidinium hydrochloride (Maniatis et al. *Molecular Cloning, A Laboratory Manual*, Cold Spring Harbor Lab., Cold Spring Harbor, N.Y. (1989)) were electrophoresed on SDS-PAGE. As a standard, purified Hsp65 was run in parallel. Hsp65-E6 expression was assessed by the appearance of a strongly Coomassie blue-staining band migrating slightly slower (apparent molecular weight (MOO) of approximately 73 kDa) than authentic Hsp65 (apparent MW of approximately 56 kDa) in samples from pET65HE6-transformed bacteria that was not present in corresponding untransformed bacteria.

Preparation of an Construct for Expression of an Hsp65-HPV16 E7 Fusion Protein in Bacteria A complete HPV16 E7-coding region was inserted at the carboxy-terminal end of the hsp65 gene in pET65H.

A primer pair for amplification of the E7 gene was synthesized on an automated oligonucleotide synthesizer and was purified using routine procedures. The forward primer included an NheI restriction site and had the nucleotide sequence 5'-AAC CCA CCT GCT AGC ATG CAT GGA GAT-3' (SEQ ID NO:6). The reverse primer included EcoRI and a stop codon and had the nucleotide sequence 5'-AGC CAT GAA TTC TTA TGG TTT CTG-3' (SEQ ID NO:7).

Figure 3:
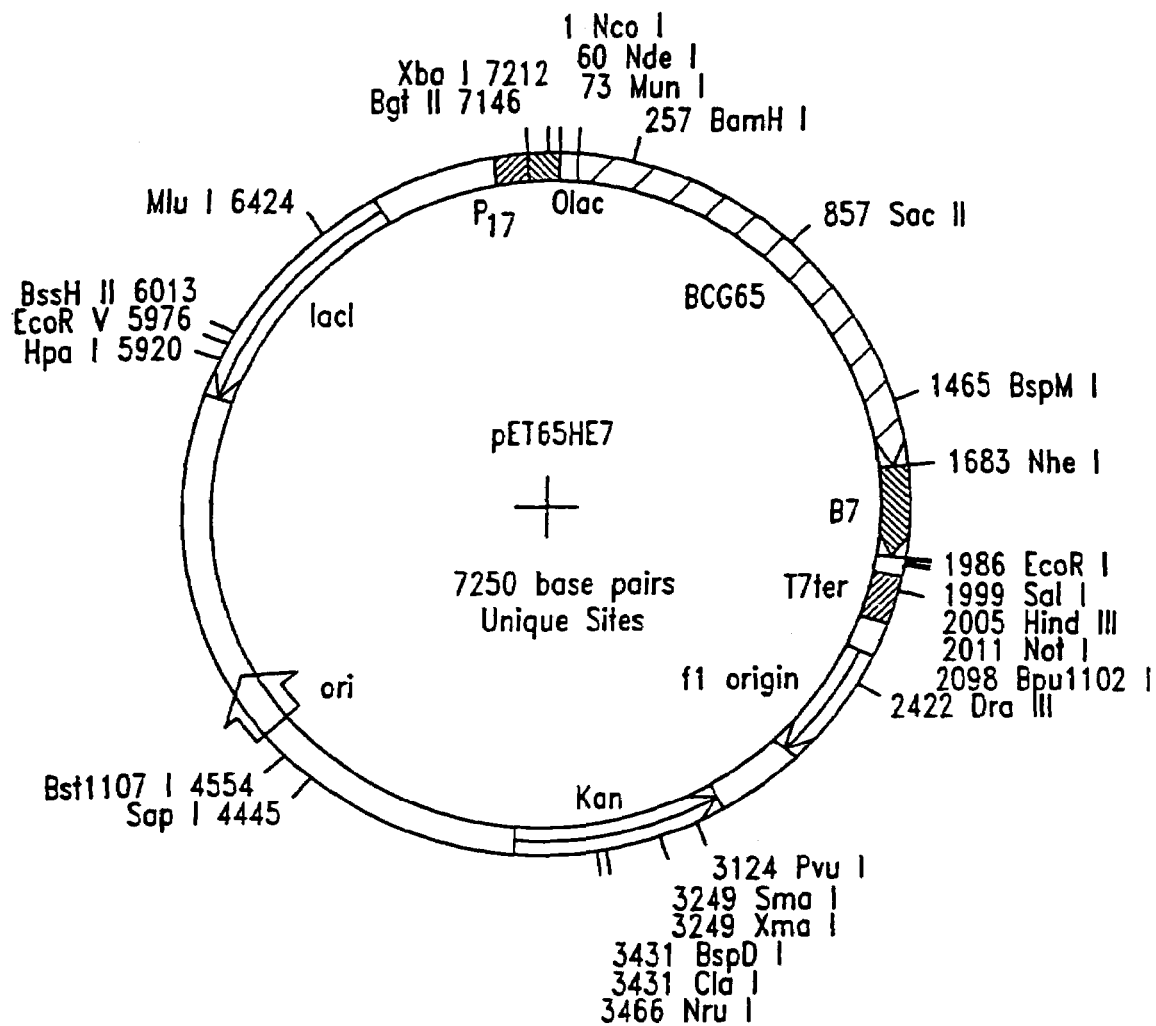
FIG. 3 is a schematic representation of construct pET65HE7.

Polymerase chain reaction (PCR) was carried out using the above primer pair and pHPV16 as the DNA template. PCR fragments were double-digested with restriction endonucleases NheI and EcoRI and ligated to NheI/EcoRI-double-digested pET65H using routine subcloning procedures. Transformation-competent cells of *E. coli* strain DH5alpha were transformed with the ligation mixture and plated out on agar containing 100 ug/ml ampicillin. Colonies of transformed cells were isolated, and plasmid DNA prepared and analyzed for the presence of the hsp65-E7 fusion gene and vector sequences by restriction mapping and nucleic acid sequencing. Correct constructs (named pET65HE7) including the hsp65-E7 fusion gene were identified and were transformed into *E. coli* strain BL21 (DE3; Invitrogen) for analysis of expression of the fusion gene. A schematic map of construct pET65HE6 is shown in FIG. 3. To test for expression of Hsp65-E7, bacteria of strain BL21 transformed with pET65HE7 were grown, induced and harvested using routine procedures. Bacteria were lysed, and soluble material as well as material solubilized from inclusion bodies by guanidinium hydrochloride were electrophoresed on SDS-PAGE and subjected to anti-E7 blot using a monoclonal antibody specific for HPV16 E7 (Zymed Laboratory Inc., catalog number 28-0006).

Example 4

Expression and Purification of Fusion Proteins

Expression and Purification of Hsp65-E6 Fusion Protein: Procedure 1

Construct pET65HE6 was transformed into *E. coli* strain BL21 (DE3; Novagen), and transformed cells were grown in 6 liter cultures of 2xYT medium (20 g Tryptone, 10 g yeast extract, 10 g NaCl per liter) containing 30 ug/ml of kanamycin at 30° C. For each culture, when the density reached 0.5 ($OD_{590}$), expression of fusion protein was induced by 0.5 mM isopropyl-thio-galactopyranoside, and the culture was incubated for an additional three hours at 37° C. Cells were harvested by centrifugation, suspended in 90 ml of lysis buffer (10 mM Tris-HCl, 0.5 mM beta-mercaptoethanol, pH 7.5) containing 200 microgram/ml lysozyme, and frozen at −70° C. One day later, the frozen cell suspension was thawed in a 37° C.-waterbath, and was supplemented with 2 microgram/ml aprotinin, 2 microgram/ml leupeptin, 2 microgram/ml pepstatin and 2 mM PMSF. All subsequent steps were performed at 0-4° C. Lysis of cells was by sonication, and insoluble material was collected by centrifugation at 17,000 rpm for 15 min (JA-17 rotor, Beckmann). Pelleted material was washed twice with lysis buffer and then solubilized, aided by sonication, in 90 ml of buffer A (50 mM Tris-HCl, pH 7.5, 6 M guanidinium hydrochloride). Insoluble material was removed by centrifugation as before. Solubilized material was then applied to a column containing 50 ml nickel-charged metal-chelating resin (Chelating Sepharose Fast Flow; Pharmacia) that had been equilibrated with buffer A. Bound fusion protein was refolded slowly on the resin with a 0-1 M NaCl gradient. The resin was washed with five volumes for buffer B (1 M NaCl) to remove residual guanidinium hydrochloride, and with five volumes of buffer C (50 mM imidazole, pH 7.5, 0.5 mM beta-mercaptoethanol, 150 mM NaCl) to remove contaminating proteins. Fusion protein was eluted with six volumes of a 50-500 mM linear imidazole gradient in buffer C. Pooled, eluted protein was dialysed overnight against approximately 40 volumes of Dulbecco's phosphate-buffered saline (2.7 mM $KH_2PO_4$, 4.3 mM $Na_2HPO_4$, 2.7 mM KCl, 0.137 M NaCl), concentrated by ultrafiltration (Amicon, 30 kDa MW cutoff) and passed through a Detoxigel resin equilibrated in Dulbecco's phosphate-buffered saline for endotoxin removal.

Expression and Purification of Hsp65-E6 Fusion Protein: Procedure 2

Construct pET65HE6 was transformed into *E. coli* strain BL21 (DE3; Novagen), and transformed cells were grown in 12 liter cultures of 2xYT medium (20 g Tryptone, 10 g yeast extract, 10 g NaCl per liter) containing 30 ug/ml of kanamycin at 30° C. For each culture, when the density reached 0.5 ($OD_{590}$), expression of fusion protein was induced by 0.5 mM isopropyl-thio-galactopyranoside, and the culture was incubated for an additional three hours at 37° C. Cells were harvested by centrifugation, suspended in 180 ml of lysis buffer (10 mM Tris-HCl, 0.5 mM beta-mercaptoethanol, pH 7.5) containing 200 ug/ml lysozyme, and frozen at −70° C. One day later, frozen cell suspension was thawed in a 37° C.-waterbath, and was supplemented with 2 microgram/ml aprotinin, 2 microgram/ml leupeptin, 2 microgram/ml pepstatin and 2 mM PMSF. All subsequent steps were performed at 0-4° C. Lysis of cells was by sonication, and insoluble material was collected by centrifugation at 17,000 rpm for 15 min (JA-17 rotor, Beckmann). Pelleted material was washed twice with lysis buffer and then solubilized, aided by sonication, in 180 ml of buffer A (50 mM Tris-HCl, pH 7.5, 6 M guanidinium hydrochloride). Insoluble material was removed by centrifugation as before. Solubilized material was then applied to a column containing 50 ml nickel-charged metal-chelating resin (Chelating Sepharose Fast Flow; Pharmacia) that had been equilibrated with buffer A. Bound protein was washed with buffer D (buffer A with 5% Triton X100) and then refolded slowly on the resin with a 0-1 M NaCl gradient. The resin was washed with five volumes of buffer E (1M NaCl, 1% Triton X 100) and five volumes of buffer B (1 M NaCl) to remove residual guanidinium hydrochloride, and with five volumes of buffer F (50 mM imidazole, pH 7.5, 0.5 mM beta-mercaptoethanol, 0.5 M NaCl, 15% glycerol) to remove contaminating proteins. Fusion protein was eluted with six volumes of a 50-500 mM linear imidazole gradient in buffer F. Pooled, eluted protein was dialysed overnight against 40 volumes of buffer G (30 mM Tris-HCl, pH 6.5, 2 mM EDTA, 5 mM beta-mercaptoethanol, 15% glycerol) and applied to a 50 ml SP-Sepharose column equilibrated in the same buffer. Fusion protein (about 42 mg, representing about 50% of total fusion protein present in unfractionated extract) was recovered in the flow-through fraction, dialysed overnight against 40 volumes of Dulbecco's phosphate-buffered saline (2.7 mM $KH_2PO_4$, 4.3 mM $Na_2HPO_4$, 2.7 mM KCl, 0.137 M NaCl), and concentrated by ultrafiltration (Amicon; 30 kDa MW cutoff).

Hsp65-E7 fusion protein was expressed and purified by the same procedures. Purity of fusion proteins was estimated by SDS-PAGE and Coomassie blue staining of gels. The proteins were typically 70-90% pure after procedure 1, and approximately 95% pure after preferred procedure 2. Endotoxin levels after purification using procedure 2 were below 20 EU/mg protein.

Example 5

Immunization with HSP65-E6 and HSP65-E7

Female C57/BI/6 mice, six to eight weeks old, were obtained from Charles River Laboratory (St. Constant, Quebec, Canada). Groups of six to eight mice per group were immunized subcutaneously in the nape of the neck with equal amounts of Hsp65-E6 and Hsp65-E7 fusion proteins in Dulbecco's phosphate-buffered saline purified as described under Example 4. Doses of total fusion proteins administered were 20 microgram or 200 microgram, respectively. Negative control immunizations were with Freund's incomplete adjuvant in saline (IFA), and positive control immunizations with 100 microgram of a synthetic HPV16 E7 peptide including residues 44 to 62 in IFA and saline. Relative to the doses of fusion proteins applied, this amount of E7 peptide administered represented a 20 or 200 fold excess, respectively. Immunizations were repeated 14 days later. Twelve days after the second immunization, mice were challenged by subcutaneous injection into a shaved back area of mice with $1.3 \times 10^5$ E7-expressing tumor cells of the line TC-1. Tumor incidence was scored as the presence or absence of tumor based on visual observation and palpation every two days for fifty days. The TC-1 tumor cell line expressing the HPV16 E7 protein was derived from primary lung cells of C57/BI/6 mice by immortalization and transformation with HPV16 E6 and E7 genes and an activated human c-Ha-ras gene as described by Lin et al. (*Cancer Res.* 56:21-26 (1996)). For tumor inoculation, TC-1 cells, supplied by Dr. T.-C. Wu (The Johns Hopkins Medical Institutions, Baltimore, Md.), were grown to 60-70% confluence in RPMI1640 medium supplemented with 10% fetal calf serum (Hyclone, Logan, Utah), nonessential amino acids, glutamine, pyruvate, gentamycin, beta-mercaptoethanol, 0.4 mg/ml Geneticin® (Life Technologies, Grand Island, N.Y.) and 0.2 mg/ml hygromycin B at 37° C. Cells were harvested by trypsinization and resuspended in Hank's buffer solution at $6.5 \times 10^5$ cells/ml.

Figure 4:
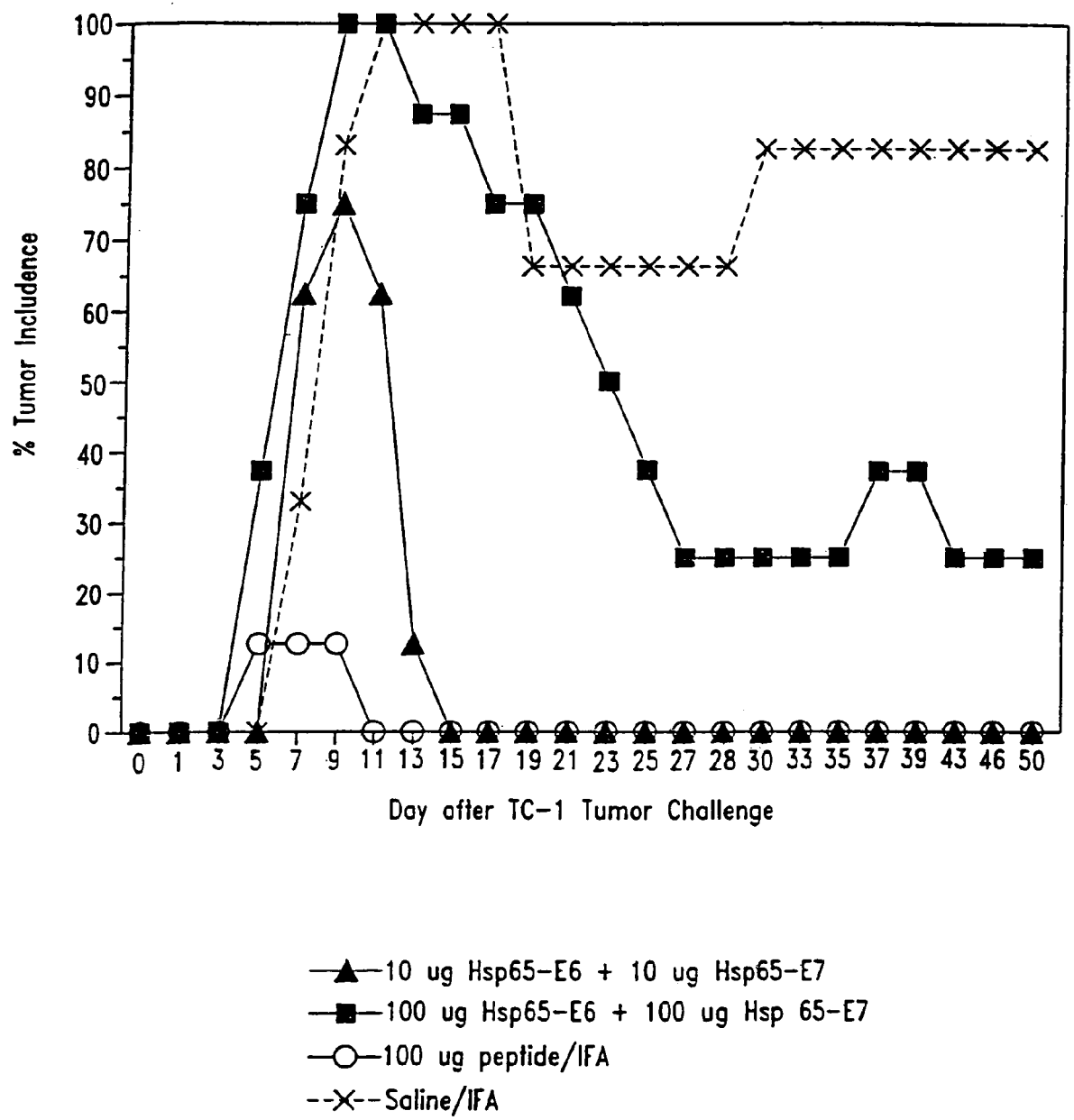
FIG. 4 is a graph of percent tumor incidence versus time after TC-1 tumor challenge, demonstrating successful immunization of mice with Hsp65-E6 and -E7 fusion proteins against the tumor.

Results of one such experiment are shown in FIG. 4. Shortly after challenge, tumor incidence rose in all treatment groups (between 5 and 15 days after challenge). While the incidence remained high for the IFA group, it dropped dramatically to 0% for groups treated with 200 microgram of fusion protein admixture or with E7 peptide in IFA. An intermediate result was obtained for the group treated with 20 microgram of fusion proteins. Thus, immunization with Hsp65-E6 and Hsp65-E7 fusion protein admixtures in the absence of any adjuvant effectively protected mice from a lethal challenge with E7-expressing tumor cells. A summary of results is shown in Table 1.

TABLE 1

RESPONSE TO A SECOND CHALLENGE WITH TC-1 TUMOR

| | Percent Tumor Incidence* | |
|---|---|---|
| Immunization Group | After 1st Challenge (Day 54) | After 2nd Challenge (Day 79) |
| IFA or None** | 83 (5/6) | 100 (4/4) |
| microgram fusion proteins | 25 (2/8) | 25 (1/4) |
| microgram fusion proteins | 0 (0/8) | 0 (0/4) |
| E7 peptide in IFA | 0 (0/8) | 0 (0/4) |

*In parentheses, the number of animals with tumor/total number of animals per group is given. In the right column, animals were monitored for the presence or absence of tumor for an additional 25 days (after 2nd challenge).
**As a control for the 2nd tumor challenge, a group of unimmunized animals was included for comparison.

Example 6

Exposure of Immunized Animals to a Second Challenge with Tumor Cells

To assess the longevity of the immune response to HPV antigens, groups of four surviving animals from the previous experiment (at day 54), both from fusion protein-treated groups and from the E7 peptide/IFA group, were challenged a second time with $1.3 \times 10^5$ live TC-1 tumor cells per animal. As a control, a group of naive mice, exposed to the same tumor challenge, was included. Tumor incidence was assessed 25 days later.

Results are shown in Table 1. Animals previously immunized with fusion proteins or with E7 peptide/IFA were completely or nearly completely protected from the second challenge, whereas unimmunized animals showed a 100% tumor incidence.

Example 7

Cytolytic Activity of Splenocytes from Immunized and Unimmunized Animals

Groups of two mice of fusion protein-, peptide- or unimmunized animals were euthanized by cervical dislocation, and their spleens were removed. Single cell suspensions of pooled spleens were prepared and washed once in Hank's buffer solution supplemented with 5% fetal calf serum. Lymphoid cells were restimulated by culturing $20 \times 10^6$ viable cells with $2 \times 10^6$ mitomycin C-treated TC-1 cells for five days in RPMI-1640 medium supplemented with 10% fetal bovine serum, 2 mM L-glutamine, 1 mM sodium pyruvate, 50 microM 2-mercaptoethanol and 50 microgram/ml gentamycin sulfate at 37° C. and 5% $CO_2$. The splenocytes (effector cells) were then harvested and used in the CTL activity assay described below.

TC-1 and HLA type-matched cell lines EL4 and MC57G not expressing an E7 epitope were used as target cells. Cells were incubated for 90 min with 150 uCi $Na_2^{51}CrO_4$ and, in the case of EL4 cells, also with 10 ug of influenza virus nucleoprotein peptide$_{366-374}$ per $10^6$ cells. Following extensive washing to remove excess radiolabel, $5 \times 10^3$ labeled target cells were co-cultured with restimulated effector cells at various effector, target cell ratios. After 4-5 hours of incubation, culture plates were centrifuged for 5 min at 200×g, and 100 ul aliquots of supernatant solutions containing radiolabel released from cells were collected into Beckman Ready Caps. Radioactivity was measured by liquid scintillation counting. To determine spontaneously released and total releasable radioactivity, supernatant solutions from cultures containing target cells only or from target cells lysed by the addition of Triton X100 were collected, and radioactivity determined as before. Results were expressed as % corrected lysis, calculated based on the following formula:

Percent Corrected Lysis=$100 \times (cpm_{test} - cpm_{spont}) / (cpm_{total} - cpm_{spont})$, wherein $cpm_{test}$ is the radioactivity released from a particular co-culture, $cpm_{spont}$ is the spontaneously released radioactivity of a target cell culture and $cpm_{total}$ is the radioactivity released by Triton X100 lysis of target cells. CTL assays were performed in triplicate, and averaged values were provided.

Figure 5:
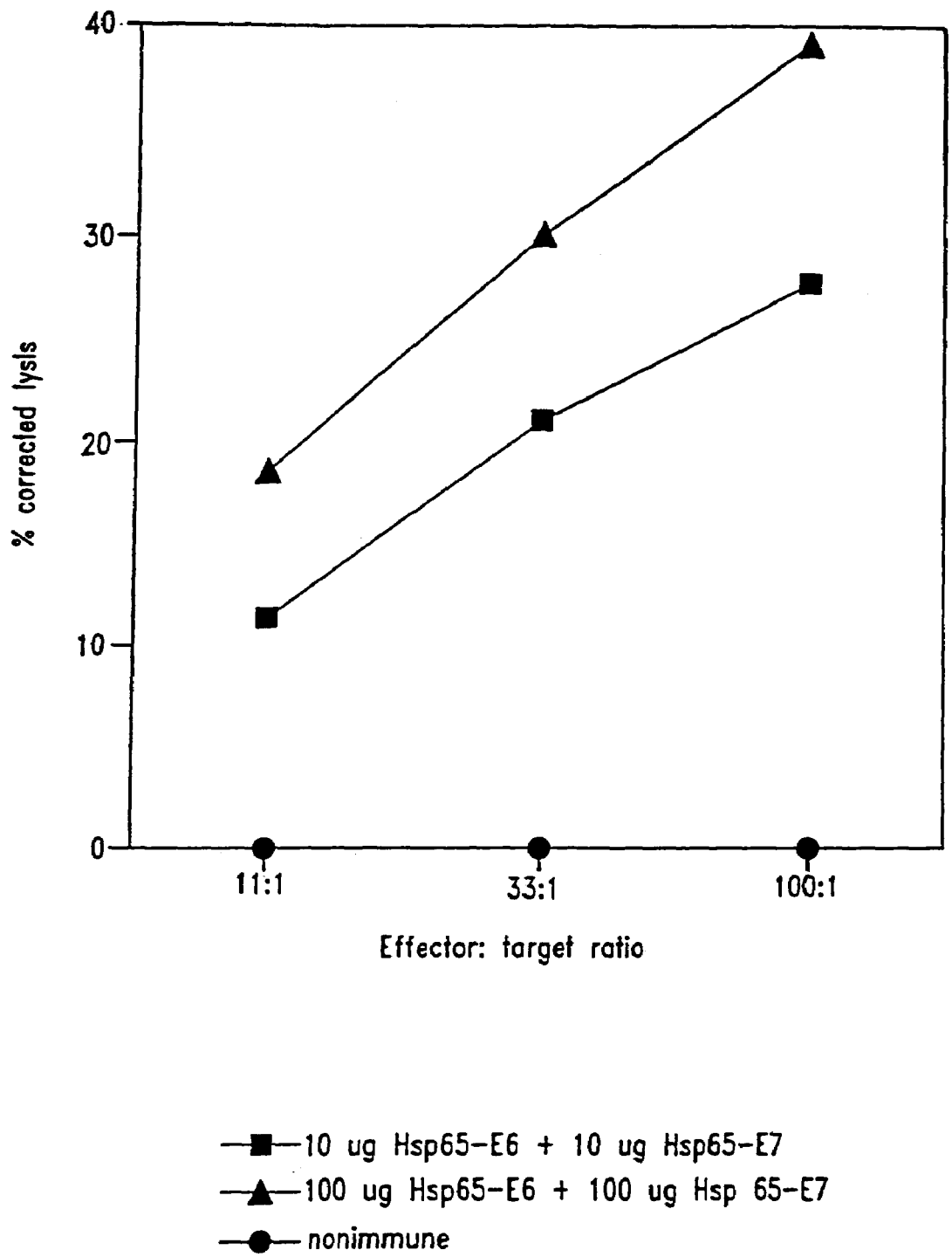
FIG. 5 is a graph of percent specific cell lysis of TC-1 tumor cells versus ratio of effector to target cells, demonstrating a cell-mediated cytolytic response against HPV antigen (E7)-expressing target tumor cells in immunized mice.

Results of an experiment using TC-1 cells as target cells is shown in FIG. 5. 40% and 25% of lysis of TC-1 cells were mediated by effector cells (used at a 100 fold excess over target cells) obtained from animals immunized with 200 microgram and 20 microgram of fusion proteins, respectively.

Figure 6:
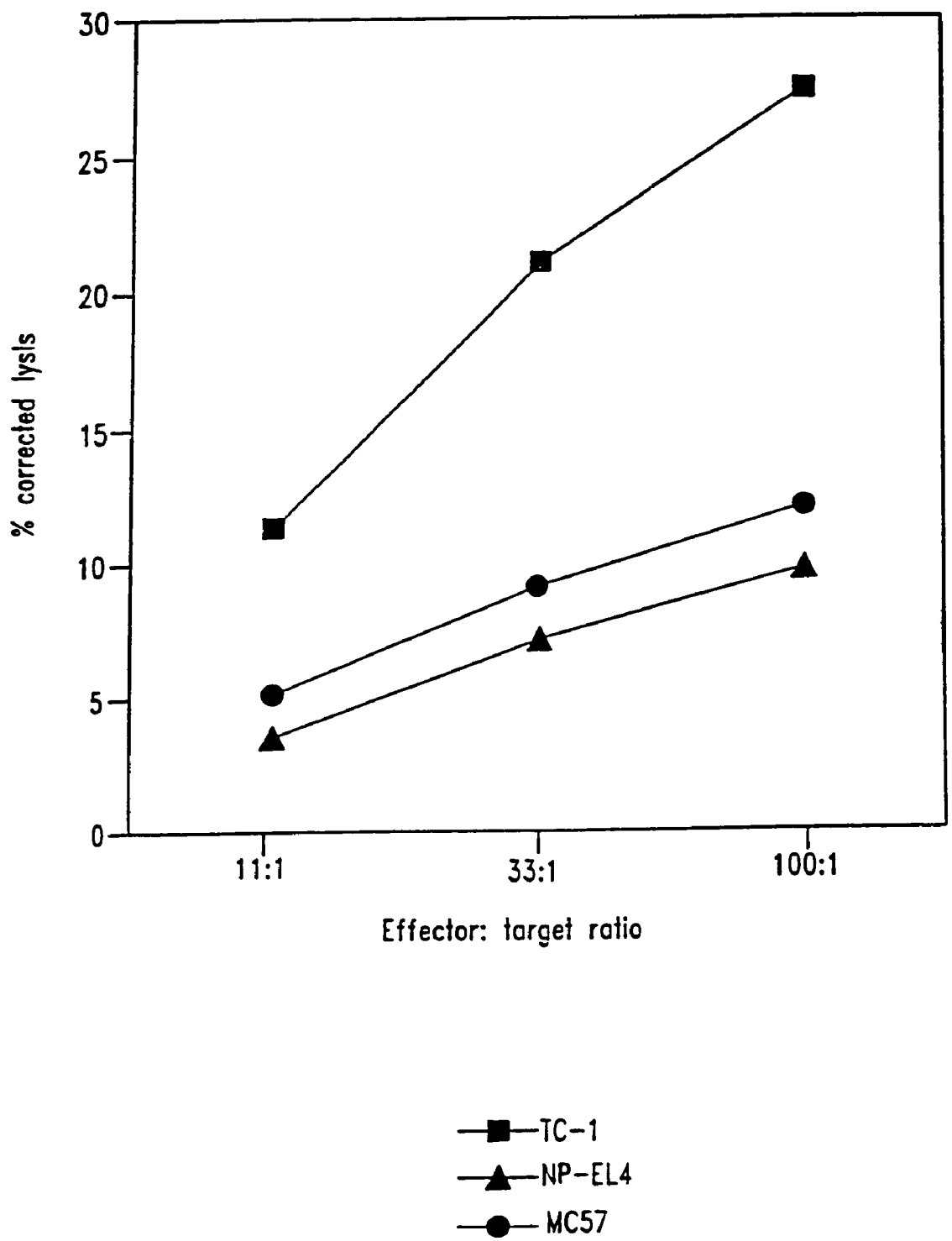
FIG. 6 is a graph of percent lysis of different target cells versus ratio of effector to target cells, demonstrating specificity of the cell-mediated cytolytic immune response against HPV E7-expressing target tumor cells in immunized mice.

In a second experiment, the specificity of CTL activity was tested using splenocytes from animals immunized with 20 microgram of fusion proteins. Results shown in FIG. 6 demonstrate effective lysis of HPV16 E6/E7-transformed TC-1 cells. Lysis of two other cell types (EL4 and MC57G) not expressing an HPV antigen occurred with a much reduced efficiency, demonstrating the specificity of the CTL response elicited by the immunization with Hsp65-E6 and -E7 fusion proteins.

Example 8

Regression of TC-1 Tumor in Mice After Treatment with HSP65-E7 Fusion Protein

Three groups of eight C57/BU6 mice were used in this experiment. Each animal was inoculated with $1.3 \times 10^5$ TC-1 cells subcutaneously into a shaved back area. Two days later, a first group was administered saline (negative control), a second group 100 microgram/animal of Hsp65-E7 fusion protein in saline and a third group 100 microgram/animal of E7 peptide in saline and IFA (positive control). All injections (0.2 ml) were given subcutaneously in the nape of the neck. Fourteen days later (16 days after tumor inoculation), injections were repeated. Beginning one day after tumor inoculation and every two days thereafter, the mice were examined for the presence or absence of tumor by visual inspection and palpation.

Figure 7:
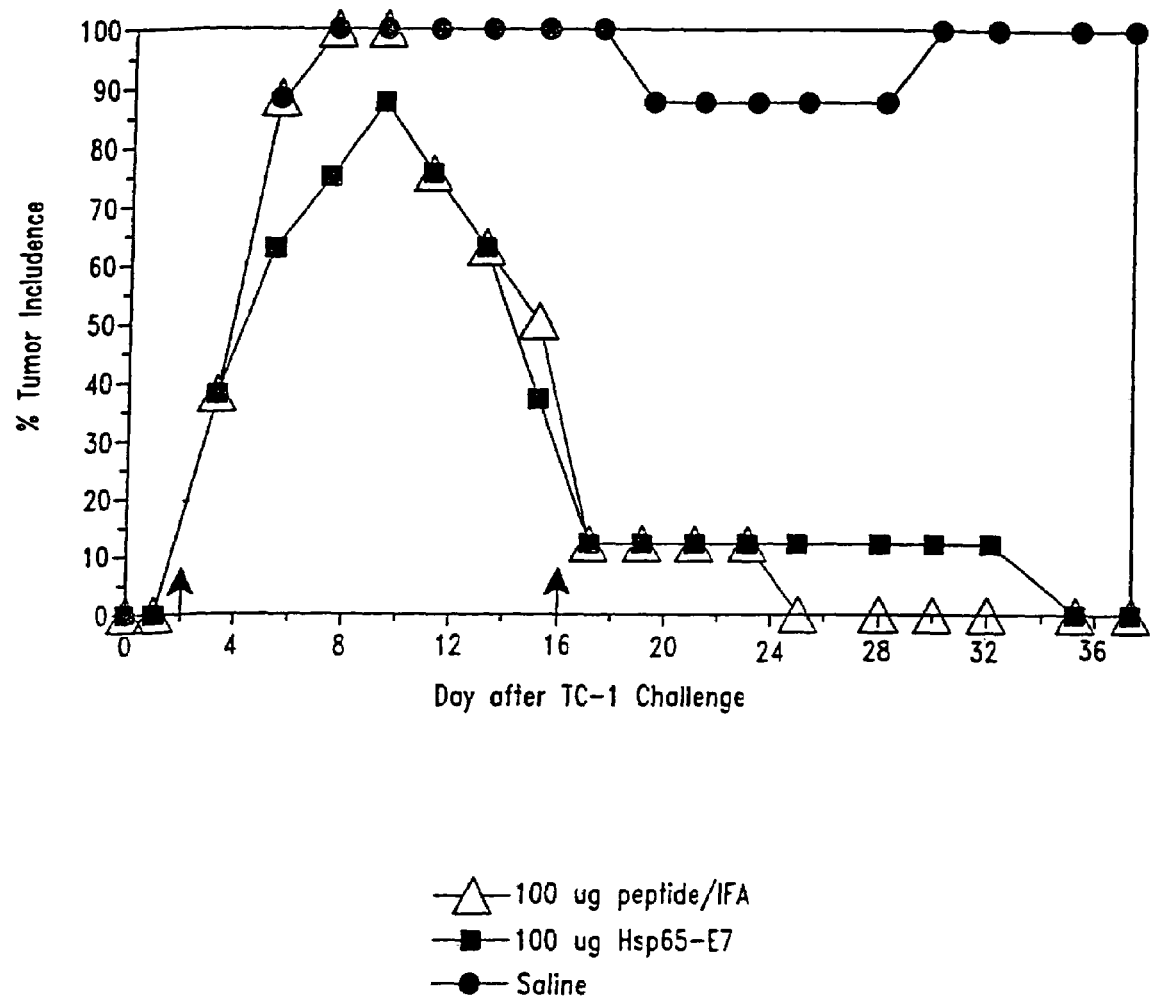
FIG. 7 is a graph of percent tumor incidence in mice administered $1.3 \times 10^5$ TC-1 tumor cells and subsequently injected with saline, Hsp65-E7 fusion protein in saline or E7 peptide in saline/IFA versus days after tumor cell administration.

FIG. 7 reveals that 9 days after tumor inoculation all of the treatment groups showed maximal tumor incidence (expressed as percentage of animals showing tumors), ranging from 85 to 100%. By day 17, however, the group treated with Hsp65-E7 fusion protein as well as the group given E7 peptide in IFA showed a highly significant decrease in tumor incidence that leveled off at about 15%. By contrast, the saline-treated group continued to have nearly 100% tumor incidence throughout the remainder of the observation period. These results demonstrate that Hsp65-E7 fusion protein, administered in the absence of adjuvant, induces drastic regression of an HPV-induced tumor.

Figure 8:
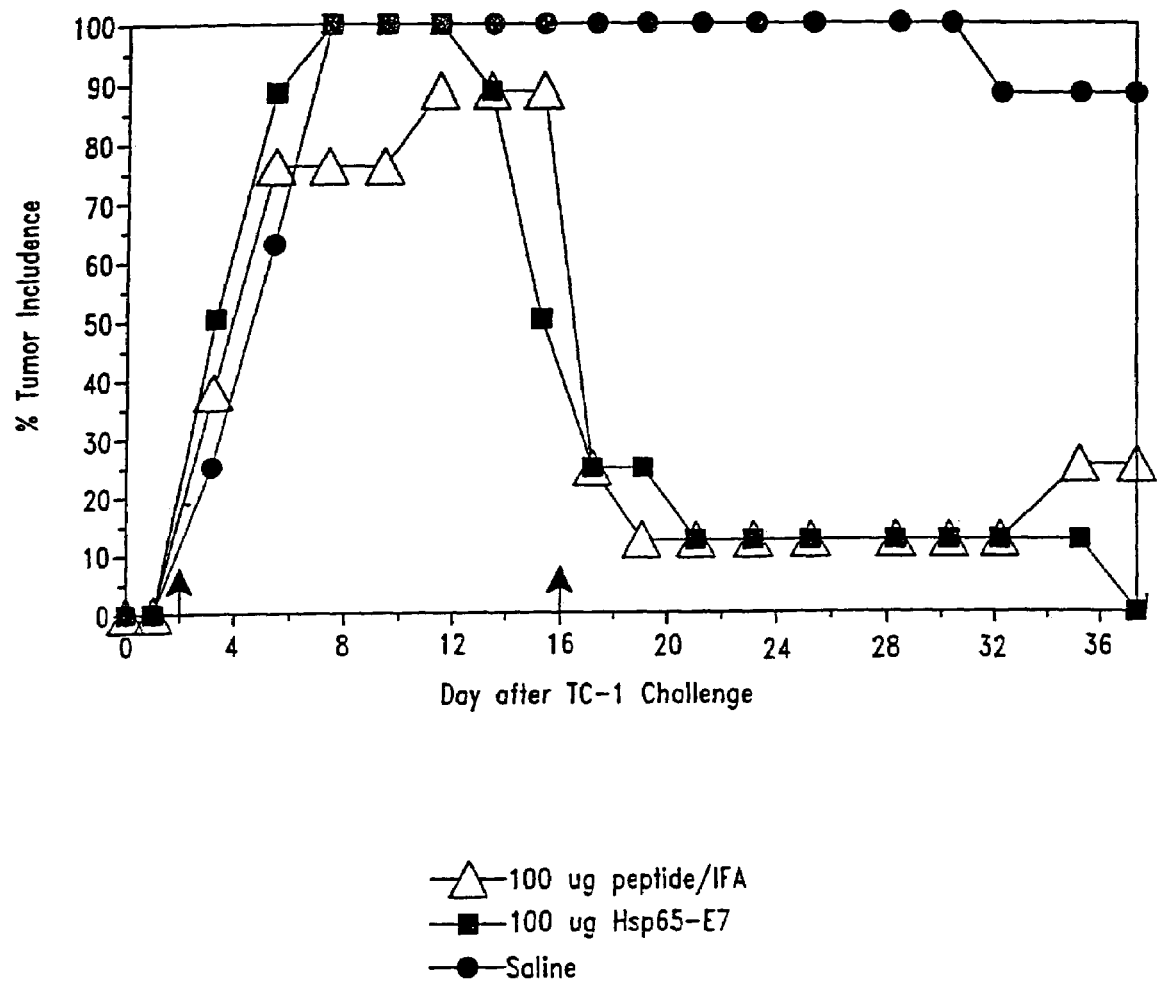
FIG. 8 is a graph of percent tumor incidence in mice administered $2 \times 10^5$ TC-1 tumor cells and subsequently injected with saline, Hsp65-E7 fusion protein in saline or E7 peptide in saline/IFA versus days after tumor cell administration.

Results from a similar experiment are shown in FIG. 8. In this experiment, animals were inoculated with a higher tumor dose ($2\times10^5$/animal) than in the previous experiment. Results obtained were closely similar to those of the previous experiment.

Example 9

Comparison of the Ability of E7 Protein and HSP65-E7 Fusion Protein to Induce Cellular Immune Responses Hsp65-E7 fusion protein was produced and purified as described in Example 4. Full length HPV E7 protein was obtained by the following procedure.

Figure 9:
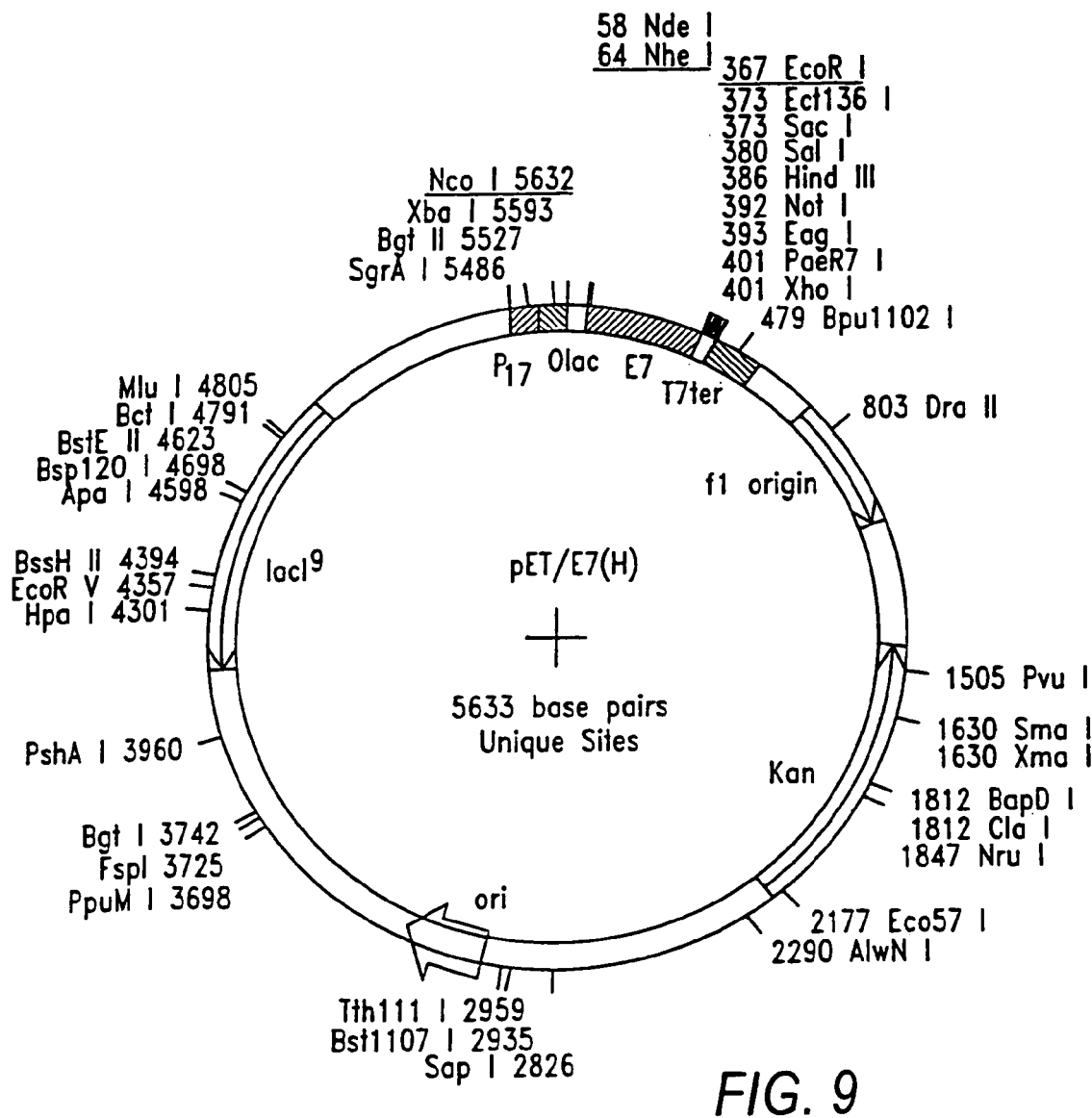
FIG. 9 is a schematic representation of construct pET/E7 (H).

The E7 gene was amplified from HPV16 genomic DNA (pSK/HPV16 obtained from the American Type Culture Collection) using AmpliTaq DNA polymerase (Perkin Elmer). The forward primer (5'-AAC CCA GCT GCT AGC ATG CAT GGA GAT-3') (SEQ ID NO:11') contained an NheI site immediately upstream of the ATG start codon, wile the reverse primer (5'-AGC CAT GAA TTC TTA TGG TTT CTG-3') (SEQ ID NO:7) contained an EcoRI site immediately downstream of the TAA stop codon of the E7-coding sequence. The PCR product was digested with NheI and EcoRI, purified from an agarose gel, and ligated to pET28a that had been digested with the same restriction enzymes. Transformation of bacteria, isolation of colonies containing recombinants, and preparation of plasmid DNA from expanded colonies containing recombinants, and preparation of plasmid DNA from expanded colonies were carried out by standard procedures. See, for example, Ausubel et al. (eds.), *Short Protocols in Molecular Biology*, 3$^{rd}$ *Edition* (John Wiley & Sons, Inc. 1995). The identity of the resulting plasmid construct, pET/E7 (H) was confirmed by diagnostic restriction digestion and DNA sequence analysis. A schematic map of pET/E7(H) is presented in FIG. 9.

Twelve liters of 2xYT medium containing 30 µg/ml kanamycin were inoculated with a culture of *E. coli* BL21 (DE3) containing pET/E7 (H) and incubated overnight at 30° C. with aeration. When an optical density of 0.5 was reached, the culture was induced with 0.5 mM IPTG for three hours. Cells were then harvested by centrifugation, resuspended in 180 ml of lysis buffer (10 mM Tris-HCl, pH 7.5, 0.5 mM 2-mercaptoethanol) supplemented with 200 µg/ml lysozyme and frozen at −70° C. overnight. Cell suspension was thawed in a 37° C. water bath in the presence of 2 µg/ml aprotinin, 2 µg/ml leupeptin, and 2 µg/ml pepstatin. Following addition of 2 mM PMSF, cell suspension was subjected to vigorous sonication, and insoluble proteins were collected by centrifugation. Protein pellets were twice resuspended in lysis buffer, resonicated and recollected by centrifugation. Protein pellets were then solubilized by sonication in buffer A (50 mM Tris-HCl, pH 7.5, 6 M guanidinium hydrochloride, 1 mM 2-mercaptoethanol), and insoluble material was removed by centrifugation. Solubilized proteins were applied to a 50 ml Ni-chelating column (2.6 cm×12 cm; Pharmacia), which had been preequilibrated in buffer A. Bound protein was washed with 5 bed volumes of buffer E (buffer A with 2% Triton X-100) and refolded with a guanidinium hydrochloride-sodium chloride gradient (0.1 M NaCl/6.0 M guanidinium hydrochloride; 5 bed volumes) in the presence of 1% Triton X-100. Refolded protein was washed with 5 bed volumes of buffer F (30 mM Tris-HCl, pH 7.5, 1 M NaCl, 15% glycerol, 2% Triton X-100, 1 mM 2-mercaptoethanol) and subsequently with 5 bed volumes of buffer G (buffer F without Triton X-100) to remove Triton X-100. The column was washed further with 5 bed volumes of buffer H (50 mM imidazole, pH 7.5, 0.5 M NaCl, 15% glycerol, 1 mM 2-mercaptoethanol) to remove weakly bound proteins. E7 protein was eluted with a linear imidazole gradient (50 mM to 1 M imidazole in buffer H). E7 protein was concentrated and dialyzed against Dulbecco's phosphate-buffered saline supplemented with 25% glycerol. Soluble protein was stored at −70° C. The E7 preparation was found to be essentially homogenous by SDS-PAGE and protein staining.

Endotoxin concentrations of the protein preparations were assessed by the *limulus* amoebocyte assay and were found to be no higher than 50 endotoxin units per milligram protein.

Figure 10:
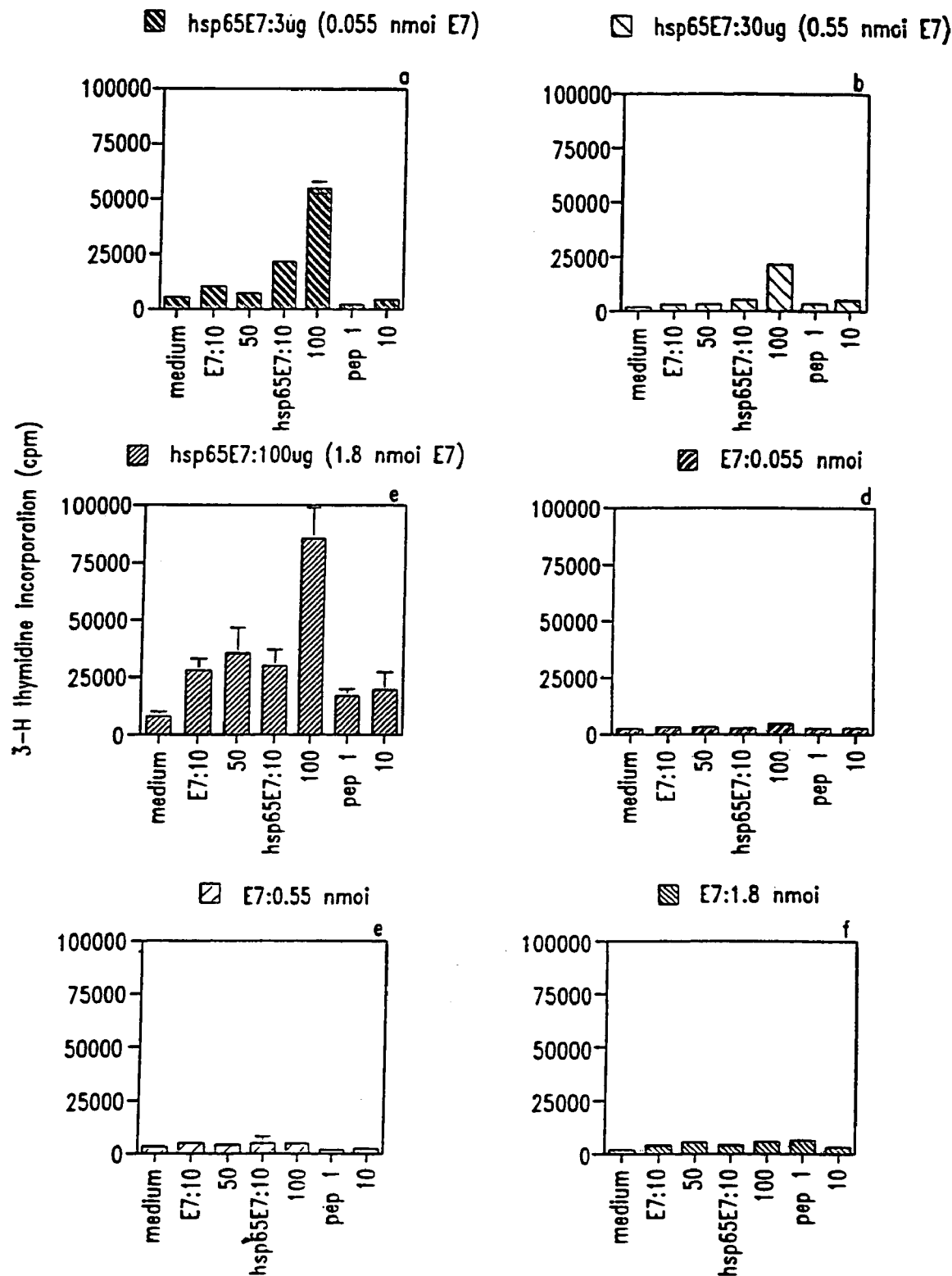
FIG. 10 is a collection of graphs showing thymidine incorporation by cultured lymph node cells obtained from mice immunized with Hsp65-E7 fusion protein or E7 protein.

Groups of five C57BL/6 mice were immunized by injection at the base of the tail with saline, or 0.055, 0.55 or 1.8 nanomoles of E7 protein or Hsp65-E7 fusion protein in saline. Injection volumes were 0.2 ml. Ten days later, inguinal lymph nodes (LN) were removed aseptically from each animal, and LN from each of the five animals of a group were pooled. Cell suspensions were prepared by a standard procedure. For each pool of LN cells ($2\times10^6$ cells/ml), flat bottom 96-well plates were seeded with $4\times10^5$ cells per well. Cells were tested in triplicate for proliferative responses to addition of either medium, 10 or 50 µg/ml E7 protein, 10 or 100 µg/ml Hsp65-E7 fusion protein, or 1 or 10 µg/ml E7 peptide ("pep"; residues 44-57). Following additions, cells were incubated for four days at 37° C. and 5% $CO_2$. Tritiated thymidine (1 µCi) was added to each culture. After 15 hours of further incubation, cells were harvested and prepared for scintillation counting. Data are presented in FIG. 10 as mean cpm of radioactivity incorporated+/− standard deviation.

The different panels show assays with LN cells from animals immunized with the different amounts of Hsp65-E7 fusion protein or E7 protein recited above. The results show that immunization with Hsp65-E7 fusion protein induces cellular immunity to the fusion protein itself (top and middle left) as well as to the E7 protein (middle left). Recognition of E7 protein is further demonstrated by the observed induction of proliferation by E7 peptide, which peptide is known to represent a T helper cell epitope (middle left). In contrast, no proliferative responses were observed with LN cells from animals immunized with different amounts of E7 protein (middle right and bottom) or mock-immunized with saline. Cells prepared from E7-protein-immunized animals were viable as evidenced by their ability to proliferate in response to T cell mitogen ConA. In summary, when compared to immunization with E7, immunization with Hsp65-E7 fusion protein elicits a superior cellular immune response to E7 as assessed by proliferation of LN cells from immunized animals.

Example 10

Figure 11:
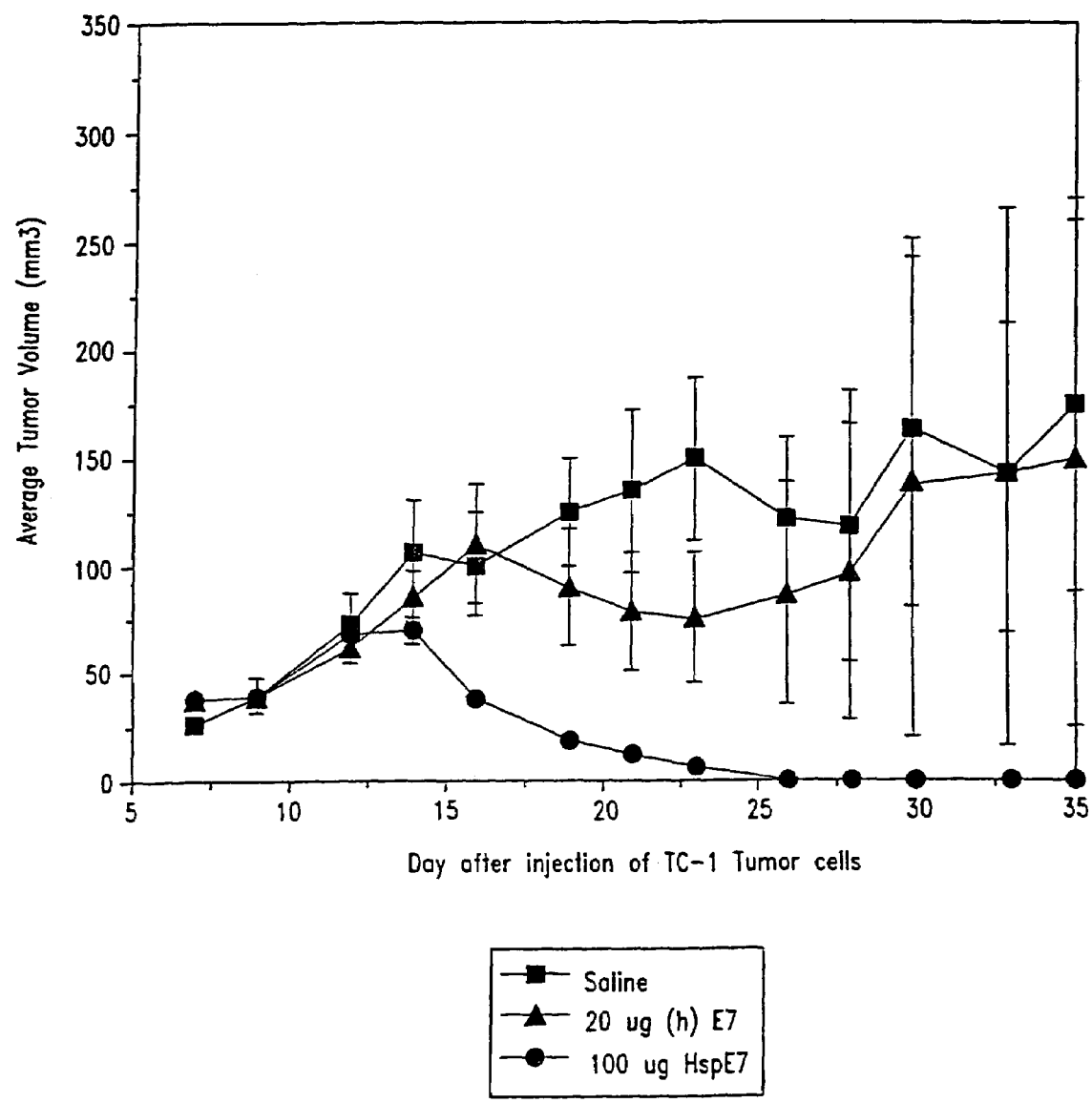
FIG. 11 is a graph showing the effect of treatment with Hsp-E7 fusion protein or E7 on tumor size in mice having TC-1 tumor cells.

Treatment with HSP65-E7 Fusion Protein Causes Regression of Sizeable Established Tumors To test the efficacy of Hsp65-E7 fusion protein in tumor therapy, C57/BL/6 mice were inoculated with $1.3 \times 10^5$ TC-1 tumor cells by subcutaneous injection into a shaved back area. Seven days later when all animals had developed palpable/measurable tumors, animals were assigned arbitrarily to three treatment groups. Each group included 12-14 animals. All treatments were by subcutaneous injection of a volume of 0.2 ml in the nape of the neck. The first group was injected with 100 µg Hsp65-E7 fusion protein, the second group with 20 µg E7 protein (corresponding to a similar molar amount as 100 µg fusion protein), and the third group with saline. Beginning one day after tumor inoculation, mice were inspected visually and by palpation for the presence of tumor. Tumor volumes were determined using calipers in two orthogonal directions. Volumes were obtained from these measurements using the conversion formula described by Naito et al., *Cancer Research* 46:4109 (1986). Results are presented in FIG. 11 as average tumor volume in each group +/–standard error.

The results demonstrate that treatment with Hsp65-E7 fusion protein resulted in complete regression of sizeable, established tumors. The effect was manifest in each of the animals treated. In contrast, neither mock treatment nor treatment with E7 protein caused more than transient regression of tumors. A statistical evaluation of tumor measurements, performed at three time points late in the experiment is presented in Table 2. As is evident from the p values calculated, the effects on tumor size of treatment with Hsp65-E7 fusion protein are statistically different from the effects of the other treatments.

TABLE 2

STATISTICAL COMPARISON OF TREATMENT GROUPS

| Comparison | Day of measurement | p Value |
|---|---|---|
| Saline vs. Hsp65-E7 | 30 | 0.048 |
|  | 33 | 0.079 |
|  | 35 | 0.046 |
| Saline vs. E7 | 30 | 0.853 |
|  | 33 | 1 |
|  | 35 | 0.86 |

Note that in the previous Examples, Hsp65-E7 protein was produced as a histidine-tagged protein. To demonstrate unambiguously that the observed therapeutic effects were not related in any way to the presence in the fusion protein of an oligo-histidine sequence, Hsp65-E7 fusion protein lacking the histidine tag was prepared and used in this Example. The fusion protein was obtained using the following procedure.

Figure 12:
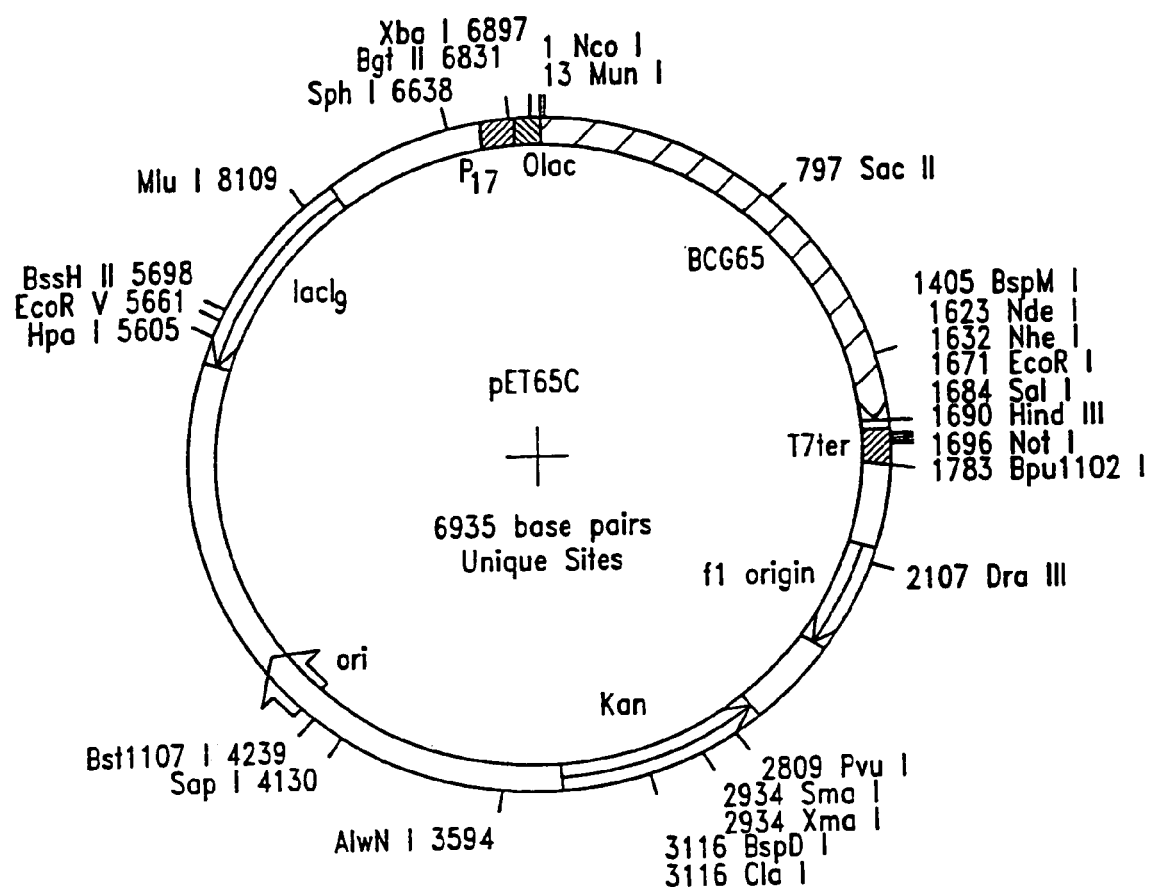
FIG. 12 is a schematic representation of construct pET65C.

For construction of plasmid pET65C (FIG. 12), the Bacillus Calmette Guerin (BCG) hsp65 gene was amplified from plasmid RIB 1300 (Van Eden et al., *Nature* 331:171, 1988) using AmpliTaq DNA polymerase (Perkin Elmer). The forward primer used (5'-TTC GCC ATG GCC AAG ACA ATT GCG-.3') (SEQ ID NO:8) contained an NcoI site that included the ATG start codon of the hsp65 gene, and the reverse primer (5'-CGC TCG GAC GCT AGC TCA CAT ATG GAA ATC CAT GCC-3') (SEQ ID NO:9) contained an NdeI site immediately upstream from the TGA stop codon of the Hsp65-coding sequence and an NheI site immediately downstream. The PCR product was digested with NdeI and NheI, purified from an agarose gel, and ligated to similarly digested pET28a. The ligation mixture was transformed into *E. coli* DH5α, and antibiotic-resistant colonies were isolated and amplified for preparation of plasmid DNA. Plasmid pET65C was identified by diagnostic restriction digests and DNA sequence analysis.

Figure 13:
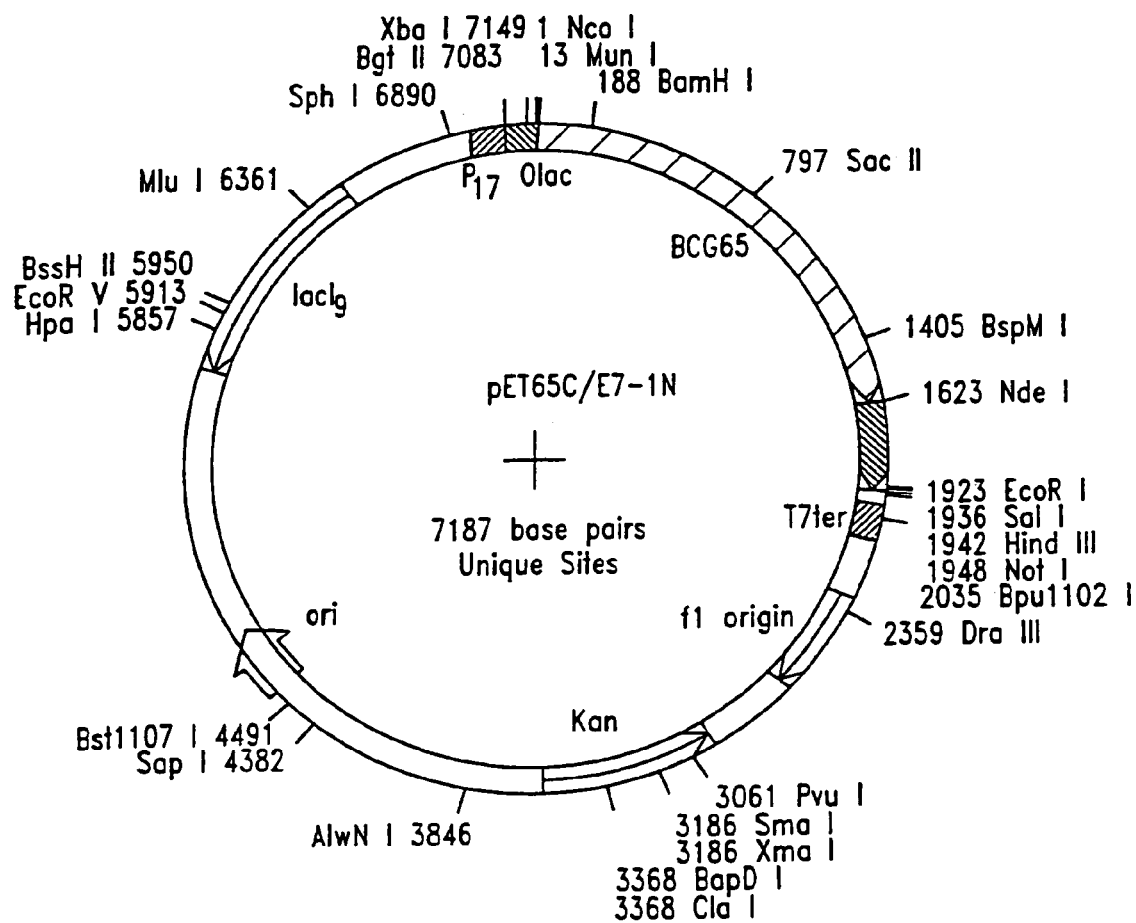
FIG. 13 is a schematic representation of construct pET65C/E7-1N.

To prepare plasmid pET65C/E7-1N containing an untagged Hsp65-E7 fusion protein gene, the E7 gene was amplified from HPV 16 genomic DNA (pSK/HPV16 obtained from the American Type Culture Collection) using AmpliTaq DNA polymerase (Perkin Elmer). The forward primer (5'-CCA GCT GTA CAT ATG CAT GGA GAT-3') (SEQ ID NO: 10) contained an NdeI site that included the ATG start codon, while the reverse primer (5'-AGC CAT GAA TTC TTA TGG TTT CTG-3') (SEQ ID NO:7) contained an EcoRI site immediately downstream of the TAA stop codon of the E7-coding sequence. The PCR product was digested with NdeI and EcoRI, purified from an agarose gel, and ligated to pET65C that had been digested with the same restriction enzymes. Transformation of bacteria, isolation of colonies containing recombinants, and preparation of plasmid DNA from expanded colonies were carried out by standard procedures. See, for example, Ausubel et al. (eds.), *Short Protocols in Molecular Biology*, 3rd Edition (John Wiley & Sons, Inc. 1995). The identity of the resulting plasmid construct, pET65C/E7-1N was confirmed by diagnostic restriction digestion and DNA sequence analysis. A schematic map of pET65C/E7-1N is presented in FIG. 13.

Twelve liters of 2xYT medium containing 30 µg/ml kanamycin were inoculated with a culture of *E. coli* BL21 (DE3) containing pET65C/E7-1N and incubated overnight at 30° C. with aeration. When an optical density of 0.5 was reached, the culture was induced with 0.5 mM IPTG for three hours. Cells were then harvested by centrifugation, resuspended in 180 ml of lysis buffer (10 mM Tris-HCl, pH 7.5, 0.5 mM 2-mercaptoethanol) supplemented with 200 µg/ml lysozyme and frozen at –70° C. overnight. Cell suspensions were thawed in a 37° C. water bath in the presence of 2 µg/ml aprotinin, 2 µg/ml leupeptin, and 2 µg/ml pepstatin. Following addition of 2 mM PMSF, cell suspensions were subjected to vigorous sonication, and insoluble proteins were removed by centrifugation. The majority of untagged Hsp65-E7 protein was found in the soluble protein fraction. To remove endotoxin, 1% Triton X-114 was added to the soluble protein fraction, and the mixture was cooled on ice (for 5 minutes or more) and mixed thoroughly. The mixture was then warmed for 10 minutes in a 30° C. water bath and then subjected to centrifugation at 24° C. The clear supernatant fraction (upper layer) was transferred into a clean tube. Centrifugation was repeated 3-6 times to remove residual Triton X-114. The supernatant fraction was then subjected to ammonium sulfate fractionation. Fusion protein was recovered in the 0-15% ammonium sulfate (w/v) fraction. Precipitated protein was dissolved in buffer B (30 mM Tris-HCl, pH 7.5, 3 M urea, 1 mM EDTA, 1 mM 2-mercaptothanol) and applied to a 170 ml Source Q column (3.5 cm×20 cm; Pharmacia) preequilibrated with buffer B. The column was washed with 3 bed volumes of buffer C (buffer B minus urea) and then with 3 bed volumes of buffer D (buffer C supplemented with 250 mM NaCl). Fusion protein was eluted with a linear salt gradient (250 mM-1 M NaCl in buffer C) (pool A) and then with 6 M guanidinium hydrochloride (buffer A) (pool B). Pool B was applied to a 50 ml Ni-chelating column (2.6 cm×12 cm; Pharmacia) preequilibrated with buffer A. Bound protein was washed with 5 bed volumes of buffer E (buffer A with 2% Titon-X-100) and refolded with a guanidinium hydrochloride-sodium chloride gradient (0.1 M NaCl/6.0 M guanidinium hydrochloride; 5 bed volumes) in the presence of 1% Triton X-100. Refolded protein was washed with 5 bed volumes of buffer F (30 mM Tris-HCl, pH 7.5, 1 M NaCl, 15% glycerol, 2% Triton X-100, 1 mM 2-mercaptoethanol) and subsequently with 5 bed volumes of buffer G (buffer F without Triton X-100) to remove Triton X-100. The column was washed further with 5 bed volumes of buffer H (50 mM imidazole, pH 7.5, 0.5 M NaCl, 15% glycerol, 1 mM 2-mercaptoethanol) to remove weakly bound proteins. Fusion protein was eluted with a linear imidazole gradient (50 mM to 1 M imidazole in buffer H). Untagged Hsp65-E7 protein was concentrated and dialyzed against Dulbecco's phosphate-buffered saline supplemented with 25% glycerol. Soluble protein was stored at −70° C.

Analysis by SDS-PAGE and protein staining revealed that the preparation was about 90% pure.

As a further demonstration of the unimportance of the histidine tag, the efficacies of histidine-tagged Hsp65-E7 and not-tagged Hsp65-E7 were directly compared in an experiment substantially identical to the one described above. The two fusion proteins were found to regress tumors with similar efficacy.

EQUIVALENTS

Those skilled in the art will know, or be able to ascertain, using no more than routine experimentation, many equivalents to the specific embodiments of the invention described herein. These and all other equivalents are intended to be encompassed by the following claims.

The invention claimed is:

1. A method of treating a tumor exhibiting an HPV protein antigen, the method comprising administering to a subject having the tumor an effective amount of an expression vector that encodes and is capable of directing expression of a fusion protein comprising the HPV protein antigen fused to a stress protein.

2. The method of claim 1, wherein the HPV protein antigen is E6 or E7.

3. A method of treating a tumor expressing an HPV protein antigen, the method comprising administering to a subject an effective amount of a composition comprising the HPV protein antigen joined to a stress protein.

4. The method of claim 1, wherein the stress protein is from the Hsp60 or the Hsp70 family.

5. The method of claim 1, wherein the stress protein is a mycobacterial stress protein.

6. The method of claim 5, wherein the mycobacterial stress protein is *M bovis* BCG hsp65.

7. The method of claim 1, wherein the stress protein is a mammalian stress protein.

8. The method of claim 1, wherein the stress protein is a bacterial stress protein.

9. The method of claim 3, wherein the stress protein is a mycobacterial stress protein.

10. The method of claim 9, wherein the mycobacterial stress protein is *M bovis* BCG hsp65.

11. The method of claim 3, wherein the stress protein is a mammalian stress protein.

12. The method of claim 3, wherein the stress protein is a bacterial stress protein.

13. The method of claim 3, wherein the HPV antigen is fused to the stress protein.

14. The method of claim 3, wherein the composition further comprises a second pharmaceutically acceptable component.

15. The method of claim 14, wherein the second pharmaceutically acceptable component is an adjuvant, a surfactant, an excipient, a carrier, a diluent, or a vehicle.

* * * * *

SEQUENCE LISTING

```
<160> NUMBER OF SEQ ID NOS: 11

<210> SEQ ID NO 1
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 1

Cys Val Gln Leu Ala Ser Asn Glu Asn Met Glu Thr Met
 1               5                  10

<210> SEQ ID NO 2
<211> LENGTH: 27
<212> TYPE: DNA
<213> ORGANISM: Artificial Sequence
<220> FEATURE:
<223> OTHER INFORMATION: Primer

<400> SEQUENCE: 2
aatcacttcc atatggccaa gacaatt                                        27

<210> SEQ ID NO 3
<211> LENGTH: 36
<212> TYPE: DNA
<213> ORGANISM: Artificial Sequence
<220> FEATURE:
<223> OTHER INFORMATION: Primer

<400> SEQUENCE: 3
cgctcggacg aattctcagc tagcgaaatc catgcc                              36

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
aaaagcagag ctagcatgca ccaaaag                                        27

<210> SEQ ID NO 5
<211> LENGTH: 24
<212> TYPE: DNA
<213> ORGANISM: Artificial Sequence
```

```
<220> FEATURE:
<223> OTHER INFORMATION: Primer

<400> SEQUENCE: 5
ctccatgaat tcttacagct gggt                                          24

<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
aacccacctg ctagcatgca tggagat                                       27

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
agccatgaat tcttatggtt tctg                                          24

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
ttcgccatgg ccaagacaat tgcg                                          24

<210> SEQ ID NO 9
<211> LENGTH: 36
<212> TYPE: DNA
<213> ORGANISM: Artificial Sequence
<220> FEATURE:
<223> OTHER INFORMATION: Primer

<400> SEQUENCE: 9
cgctcggacg ctagctcaca tatggaaatc catgcc                             36

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
ccagctgtac atatgcatgg agat                                          24

<210> SEQ ID NO 11
<211> LENGTH: 27
<212> TYPE: DNA
<213> ORGANISM: Artificial Sequence
<220> FEATURE:
<223> OTHER INFORMATION: Primer

<400> SEQUENCE: 11
aacccagctg ctagcatgca tggagat                                       27
```